(12) United States Patent
Mason et al.

(10) Patent No.: US 11,087,865 B2
(45) Date of Patent: Aug. 10, 2021

(54) SYSTEM AND METHOD FOR USE OF TREATMENT DEVICE TO REDUCE PAIN MEDICATION DEPENDENCY

(71) Applicant: ROM TECHNOLOGIES, INC., Brookfield, CT (US)

(72) Inventors: Steven Mason, Las Vegas, NV (US); Daniel Posnack, Fort Lauderdale, FL (US); Peter Arn, Roxbury, CT (US); Wendy Para, Las Vegas, NV (US); S. Adam Hacking, Nashua, NH (US); Micheal Mueller, Oil City, PA (US); Joseph Guaneri, Merrick, NY (US); Jonathan Greene, Denver, CO (US)

(73) Assignee: ROM Technologies, Inc., Brookfield, CT (US)

( * ) Notice: Subject to any disclaimer, the term of this patent is extended or adjusted under 35 U.S.C. 154(b) by 0 days.

(21) Appl. No.: 17/147,295

(22) Filed: Jan. 12, 2021

(65) Prior Publication Data

US 2021/0134419 A1 May 6, 2021

Related U.S. Application Data

(63) Continuation-in-part of application No. 17/021,895, filed on Sep. 15, 2020.
(Continued)

(51) Int. Cl.
*G06N 3/08* (2006.01)
*G16H 20/10* (2018.01)
(Continued)

(52) U.S. Cl.
CPC ............ *G16H 20/10* (2018.01); *G06F 3/048* (2013.01); *G06N 3/08* (2013.01); *G16H 20/30* (2018.01); *G16H 40/67* (2018.01)

(58) Field of Classification Search
CPC ........ G16H 20/10; G16H 20/30; G16H 40/67; G06F 3/048; G06N 3/08
See application file for complete search history.

(56) References Cited

U.S. PATENT DOCUMENTS

| 6,182,029 B1 | 1/2001 | Friedman |
| 6,413,190 B1 | 7/2002 | Wood et al. |

(Continued)

FOREIGN PATENT DOCUMENTS

| CA | 2698078 A1 | 3/2010 |
| CN | 112603295 A | 2/2003 |
| WO | 2019204876 A1 | 4/2019 |

*Primary Examiner* — George Manuel
(74) *Attorney, Agent, or Firm* — Dickinson Wright, PLLC; Stephen A. Mason; Jonathan H. Harder

(57) ABSTRACT

Systems, methods, and computer-readable mediums for modifying, by an artificial intelligence engine, a treatment plan for optimizing patient outcome and pain levels during treatment sessions. The system includes, in one implementation, a treatment apparatus, a patient interface, and a computing device. The treatment apparatus is configured to be manipulated by a patient while the patient performs the treatment sessions. The computing device is configured to receive the treatment plan for the patient and treatment data pertaining to the patient. The computing device is also configured to receive patient input from the patient interface correlating with the pain levels of the patient. The computing device is further configured to use the treatment plan, the treatment data, and the patient input to generate at least one threshold. Responsive to an occurrence of exceeding the at least one threshold, the computing device is configured to modify the treatment plan.

30 Claims, 11 Drawing Sheets

Related U.S. Application Data

(60) Provisional application No. 62/910,232, filed on Oct. 3, 2019.

(51) Int. Cl.

*G06F 3/048* (2013.01)
  *G16H 20/30* (2018.01)
  *G16H 40/67* (2018.01)

(56) References Cited

U.S. PATENT DOCUMENTS

| | | |
|---|---|---|
| 6,491,649 B1 | 12/2002 | Ombrellaro |
| 7,169,085 B1 | 1/2007 | Killin et al. |
| 7,209,886 B2 | 4/2007 | Kimmel |
| 7,974,689 B2 | 7/2011 | Volpe et al. |
| 8,751,264 B2 | 6/2014 | Beraja et al. |
| 8,823,448 B1 | 9/2014 | Shen |
| 9,311,789 B1 | 4/2016 | Gwin |
| 9,939,784 B1 | 4/2018 | Berardinelli |
| 10,130,298 B2 | 11/2018 | Mokaya et al. |
| 10,424,033 B2 | 9/2019 | Romeo |
| 2003/0036683 A1 | 2/2003 | Kehr et al. |
| 2006/0064329 A1 | 3/2006 | Abolfathi et al. |
| 2008/0269792 A1* | 10/2008 | Collins .................. A61H 39/08 606/189 |
| 2009/0011907 A1 | 1/2009 | Radow et al. |
| 2009/0070138 A1 | 3/2009 | Langheier et al. |
| 2010/0268304 A1 | 10/2010 | Matos |
| 2011/0172059 A1 | 7/2011 | Watterson et al. |
| 2011/0218814 A1 | 9/2011 | Coats |
| 2012/0065987 A1 | 3/2012 | Farooq et al. |
| 2012/0190502 A1 | 7/2012 | Paulus et al. |
| 2012/0310667 A1 | 12/2012 | Altman et al. |
| 2013/0123667 A1 | 5/2013 | Komatireddy et al. |
| 2013/0296987 A1 | 11/2013 | Rogers et al. |
| 2014/0006042 A1 | 1/2014 | Keefe et al. |
| 2014/0188009 A1 | 7/2014 | Lange et al. |
| 2014/0194250 A1 | 7/2014 | Reich et al. |
| 2014/0257837 A1 | 9/2014 | Walker et al. |
| 2014/0322686 A1 | 10/2014 | Kang |
| 2015/0088544 A1 | 3/2015 | Goldberg |
| 2015/0161331 A1 | 6/2015 | Oleynik |
| 2015/0339442 A1 | 11/2015 | Oleynik |
| 2016/0140319 A1 | 5/2016 | Stark et al. |
| 2016/0166881 A1 | 6/2016 | Ridgel et al. |
| 2016/0275259 A1 | 9/2016 | Nolan et al. |
| 2016/0302721 A1 | 10/2016 | Wiedenhoefer et al. |
| 2017/0004260 A1 | 1/2017 | Moturu et al. |
| 2017/0143261 A1 | 5/2017 | Wiedenhoefer et al. |
| 2017/0147789 A1 | 5/2017 | Wiedenhoefer et al. |
| 2017/0181698 A1 | 6/2017 | Wiedenhoefer et al. |
| 2017/0243028 A1 | 8/2017 | LaFever et al. |
| 2017/0278209 A1 | 9/2017 | Olsen et al. |
| 2017/0300654 A1 | 10/2017 | Stein et al. |
| 2017/0329917 A1 | 11/2017 | McRaith et al. |
| 2017/0344726 A1 | 11/2017 | Duffy et al. |
| 2017/0360586 A1 | 12/2017 | Dempers et al. |
| 2018/0052962 A1 | 2/2018 | Van Der Koijk et al. |
| 2018/0085615 A1 | 3/2018 | Astolfi et al. |
| 2018/0102190 A1 | 4/2018 | Hogue et al. |
| 2018/0240552 A1 | 8/2018 | Tuyl et al. |
| 2018/0271432 A1 | 9/2018 | Auchinleck et al. |
| 2018/0280784 A1 | 10/2018 | Romeo et al. |
| 2018/0330824 A1 | 11/2018 | Athey et al. |
| 2019/0019578 A1 | 1/2019 | Vaccaro |
| 2019/0066832 A1 | 2/2019 | Kang et al. |
| 2019/0167988 A1 | 6/2019 | Shahriari et al. |
| 2020/0143922 A1 | 5/2020 | Chekroud et al. |
| 2020/0151595 A1 | 5/2020 | Jayalath et al. |
| 2020/0152339 A1 | 5/2020 | Pulitzer et al. |
| 2020/0160198 A1 | 5/2020 | Reeves et al. |
| 2020/0176098 A1 | 6/2020 | Lucas et al. |
| 2020/0293712 A1 | 9/2020 | Potts et al. |
| 2020/0401224 A1 | 12/2020 | Cotton |

\* cited by examiner

SYSTEM AND METHOD FOR USE OF TREATMENT DEVICE TO REDUCE PAIN MEDICATION DEPENDENCY

CROSS-REFERENCES TO RELATED APPLICATIONS

This application is a continuation-in-part of U.S. patent application Ser. No. 17/021,895, filed Sep. 15, 2020, titled "Telemedicine for Orthopedic Treatment," which claims priority to and the benefit of U.S. Provisional Patent Application Ser. No. 62/910,232, filed Oct. 3, 2019, titled "Telemedicine for Orthopedic Treatment," the entire disclosures of which are hereby incorporated by reference for all purposes.

TECHNICAL FIELD

This disclosure relates generally to a system and a method for use of a treatment device to reduce pain medication dependency.

BACKGROUND

The opioid epidemic refers to the growing number of hospitalizations and deaths caused by people abusing opioids, including prescription drugs, illicit drugs, and analogues drugs. Annually in the United States, approximately 40,000 people die from an accidental overdose of opioids. Opioids, such as morphine, OxyContin, Vicodin, codeine, fentanyl, and the like, are drugs that are often used to relieve pain. Opioids are highly addictive drugs and can cause biochemical changes in the brains of people after continued use. Most people suffering from an opioid addiction initially began taking the drugs after they received, from a doctor, a prescription for pain medication (e.g., opioids) to alleviate pain resulting from an injury or a surgery. As patients engage in rehabilitation, their pain levels increase, which often leads to the patients taking more pain medication. In addition, the increased pain levels may discourage the patients from diligently following their rehabilitation treatment plans. Such noncompliance may slow down the recovery progresses of the patients, leading to patients taking pain medication for longer time periods. As the quantity and the length of time (e.g., days, weeks, months, etc.) increases for which patients take their pain medication, the more likely the patients will become addicted to and/or dependent on opioids. For example, patients may become physically dependent on opioids and experience symptoms of tolerance (i.e., patients' bodies become desensitized to the drugs and patients need to take higher doses of the drug to relieve pain) and withdrawal (e.g., physical effects). Furthermore, patients may become mentally dependent on the opioids (i.e., the use of the opioids is a conditioned response to a feeling—a trigger—and the trigger sets off biochemical changes in the patients' brains that strongly influence addictive behavior).

Remote medical assistance, also referred to, inter alia, as remote medicine, telemedicine, telemed, telmed, tel-med, or telehealth, is an at least two-way communication between a healthcare professional or professionals, such as a physician or a physical therapist, and a patient using audio and/or audiovisual and/or other sensorial or perceptive (e.g., tactile, gustatory, haptic, pressure-sensing-based or electromagnetic (e.g., neurostimulative)) communications (e.g., via a computer, a smartphone, or a tablet). The patient may use a patient interface in communication with an assistant interface for receiving the remote medical assistance via audio, visual, audiovisual, or other communications described elsewhere herein. Any reference herein to any particular sensorial modality shall be understood to include and to disclose by implication a different one or more sensory modalities.

Doctors typically prescribe opioids to a patient after conducting a physical examination and/or communicating with the patient (e.g., to obtain the patient's rehabilitative progress and/or pain level). Telemedicine is an option for healthcare professionals to communicate with patients and provide patient care when the patients do not want to or cannot easily go to the healthcare professionals' offices. Telemedicine, however, has substantive limitations as the healthcare professionals cannot conduct physical examinations of the patients. Rather, the healthcare professionals must rely on verbal communication and/or limited remote observation of the patients.

SUMMARY

In general, the present disclosure provides a system and a method for use of a treatment device to reduce pain medication dependency.

An aspect of the disclosed embodiments includes a computer-implemented system. The computer-implemented system includes, in one example, a treatment apparatus, a patient interface, and a computing device. The treatment apparatus is configured to be manipulated by a patient while the patient performs one or more treatment sessions. The patient interface includes an output device and an input device. The input device is configured to receive patient input correlating with at least one pain level of the patient during the one or more treatment sessions. The computing device is configured to receive a treatment plan for the patient. The treatment plan includes one or more exercise routines for the patient to complete on the treatment apparatus during the one or more treatment sessions. The computing device is further configured to receive treatment data pertaining to the patient. The computing device is also configured to receive patient input from the patient interface. The computing device is further configured to use the treatment plan, the treatment data, and the patient input to generate at least one threshold. Responsive to an occurrence of exceeding the at least one threshold, the computing device is configured to modify the treatment plan using an artificial intelligence engine.

Another aspect of the disclosed embodiments includes a method for modifying, by an artificial intelligence engine, a treatment plan for optimizing patient outcome and pain levels during one or more treatment sessions. The method includes receiving the treatment plan for a patient. The treatment plan includes one or more exercise routines for the patient to complete during the one or more treatment sessions. The method also includes receiving treatment data pertaining to the patient and receiving patient input correlating with at least one of the pain levels of the patient. The method further includes using the treatment plan, the treatment data, and the patient input to generate at least one threshold. Responsive to an occurrence of exceeding the at least one threshold, the method includes modifying the treatment plan.

Another aspect of the disclosed embodiments includes a tangible, non-transitory computer-readable medium storing instructions that, when executed, cause a processing device to receive a treatment plan for a patient. The treatment plan includes one or more exercise routines for the patient to complete during one or more treatment sessions. The instructions also cause the processing device to receive treatment data pertaining to the patient and receive patient input correlating with at least one pain level of the patient during the one or more treatment sessions. The instructions further cause the processing device to use the treatment plan, the treatment data, and the patient input to generate at least one threshold. Responsive to an occurrence of exceeding the at least one threshold, the instructions cause the processing device to modify the treatment plan.

Another aspect of the disclosed embodiments includes a system for modifying, by an artificial intelligence engine, a treatment plan for optimizing patient outcome and pain levels during one or more treatment sessions. The system includes, in one example, a memory device and a processing device. The memory device stores instructions. The processing device is communicatively coupled to the memory device. The processing device executes the instructions to receive a treatment plan for a patient. The treatment plan includes one or more exercise routines for the patient to complete during the one or more treatment sessions. The processing device also executes the instructions to receive treatment data pertaining to the patient and receive patient input correlating with at least one of the pain levels of the patient. The processing device further executes the instructions to use the treatment plan, the treatment data, and the patient input to generate at least one threshold. Responsive to an occurrence of exceeding the at least one threshold, the processing device executes the instructions to modify the treatment plan.

Other technical features may be readily apparent to one skilled in the art from the following figures, descriptions, and claims.

BRIEF DESCRIPTION OF THE DRAWINGS

For a more complete understanding of this disclosure and its advantages, reference is now made to the following description, taken in conjunction with the accompanying drawings. It is emphasized that, according to common practice, the various features of the drawings are not to-scale. On the contrary, the dimensions of the various features are arbitrarily expanded or reduced for clarity.

NOTATION AND NOMENCLATURE

Figure 1:
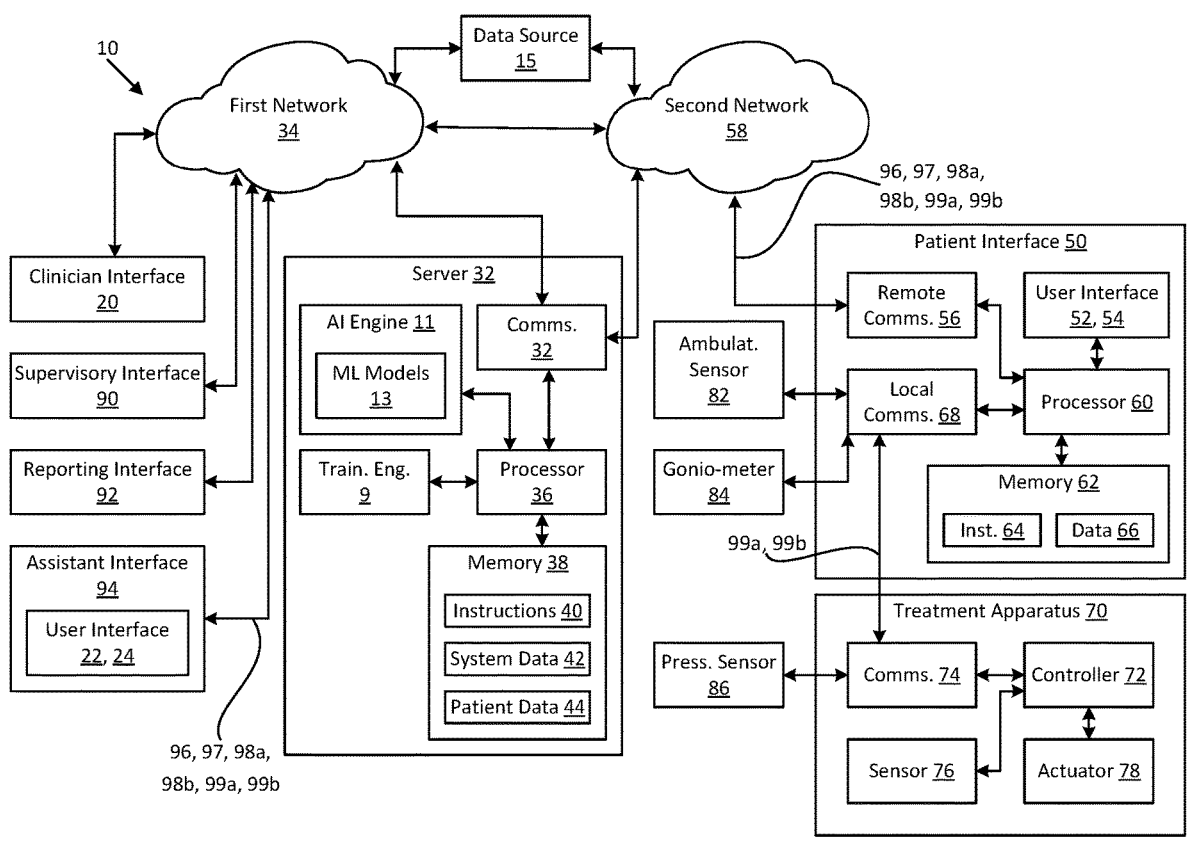
FIG. 1 generally illustrates a block diagram of an embodiment of a computer-implemented system for managing a treatment plan according to principles of the present disclosure.

Various terms are used to refer to particular system components. Different companies may refer to a component by different names—this document does not intend to distinguish between components that differ in name but not function. In the following discussion and in the claims, the terms "including" and "comprising" are used in an open-ended fashion, and thus should be interpreted to mean "including, but not limited to . . . ." Also, the term "couple" or "couples" is intended to mean either an indirect or direct connection. Thus, if a first device couples to a second device, that connection may be through a direct connection or through an indirect connection via other devices and connections.

The terminology used herein is for the purpose of describing particular example embodiments only, and is not intended to be limiting. As used herein, the singular forms "a," "an," and "the" may be intended to include the plural forms as well, unless the context clearly indicates otherwise. The method steps, processes, and operations described herein are not to be construed as necessarily requiring their performance in the particular order discussed or illustrated, unless specifically identified as an order of performance. It is also to be understood that additional or alternative steps may be employed.

The terms first, second, third, etc. may be used herein to describe various elements, components, regions, layers and/or sections; however, these elements, components, regions, layers and/or sections should not be limited by these terms. These terms may be only used to distinguish one element, component, region, layer, or section from another region, layer, or section. Terms such as "first," "second," and other numerical terms, when used herein, do not imply a sequence or order unless clearly indicated by the context. Thus, a first element, component, region, layer, or section discussed below could be termed a second element, component, region, layer, or section without departing from the teachings of the example embodiments. The phrase "at least one of," when used with a list of items, means that different combinations of one or more of the listed items may be used, and only one item in the list may be needed. For example, "at least one of: A, B, and C" includes any of the following combinations: A, B, C, A and B, A and C, B and C, and A and B and C. In another example, the phrase "one or more" when used with a list of items means there may be one item or any suitable number of items exceeding one.

Spatially relative terms, such as "inner," "outer," "beneath," "below," "lower," "above," "upper," "top," "bottom," "inside," "outside," "contained within," "superimposing upon," and the like, may be used herein. These spatially relative terms can be used for ease of description to describe one element's or feature's relationship to another element(s) or feature(s) as illustrated in the figures. The spatially relative terms may also be intended to encompass different orientations of the device in use, or operation, in addition to the orientation depicted in the figures. For example, if the device in the figures is turned over, elements described as "below" or "beneath" other elements or features would then be oriented "above" the other elements or features. Thus, the example term "below" can encompass both an orientation of above and below. The device may be otherwise oriented (rotated 90 degrees or at other orientations) and the spatially relative descriptions used herein interpreted accordingly.

A "treatment plan" may include one or more treatment protocols, and each treatment protocol includes one or more treatment sessions. Each treatment session comprises several session periods, with each session period including a particular exercise for treating the body part of the patient. For example, a treatment plan for post-operative rehabilitation after a knee surgery may include an initial treatment protocol with twice daily stretching sessions for the first 3 days after surgery and a more intensive treatment protocol with active exercise sessions performed 4 times per day starting 4 days after surgery. A treatment plan may also include information pertaining to a medical procedure to perform on the patient, a treatment protocol for the patient using a treatment device, a diet regimen for the patient, a medication regimen for the patient, a sleep regimen for the patient, additional regimens, or some combination thereof.

The terms telemedicine, telehealth, telemed, teletherapeutic, telemedicine, etc. may be used interchangeably herein.

DETAILED DESCRIPTION

The following discussion is directed to various embodiments of the present disclosure. Although one or more of these embodiments may be preferred, the embodiments disclosed should not be interpreted, or otherwise used, as limiting the scope of the disclosure, including the claims. In addition, one skilled in the art will understand that the following description has broad application, and the discussion of any embodiment is meant only to be exemplary of that embodiment, and not intended to intimate that the scope of the disclosure, including the claims, is limited to that embodiment.

As patients engage in rehabilitation, their pain levels often increase. Patients may take more pain medication as their pain levels increase. In addition, the increased pain levels may discourage the patients from diligently following their rehabilitation treatment plans. Such noncompliance may slow down the recovery progresses of the patients, resulting with patient taking pain medication for longer periods of time. As the quantity and the length of time (e.g., days, weeks, months, etc.) increases for which patients take their pain medication, the more likely the patients will become addicted to and/or dependent on their pain medication. For example, patients may become physically dependent on opioids and experience symptoms of tolerance (i.e., patients' bodies become desensitized to the drugs and patients need to take higher doses of the drug to relieve pain) and withdrawal (e.g., physical effects). Furthermore, patients may become mentally dependent on the opioids (i.e., the use of the opioids is a conditioned response to a feeling—a trigger— and the trigger sets off biochemical changes in the patients' brains that strongly influence addictive behavior). Prescribing an optimal type and quantity of pain medication for an optimal length of time can be challenging, especially when doctors are not provided with adequate patient input (e.g., a patient's pain level before, during, and after a rehabilitation session) as the patient rehabilitates. It may be desirable to modify a treatment plan for optimizing patient outcome and pain levels during one or more treatment sessions.

Determining optimal remote examination procedures to create a treatment plan for a patient having certain characteristics (e.g., vital-sign or other measurements; performance; demographic; psychographic; geographic; diagnostic; measurement- or test-based; medically historic; behavioral historic; cognitive; etiologic; cohort-associative; differentially diagnostic; surgical, physically therapeutic, pharmacologic and other treatment(s) recommended; etc.) may be a technically challenging problem. For example, a multitude of information may be considered when determining a treatment plan, which may result in inefficiencies and inaccuracies in the treatment plan selection process. In a rehabilitative setting, some of the multitude of information considered may include characteristics of the patient such as personal information, performance information, and measurement information. The personal information may include, e.g., demographic, psychographic or other information, such as an age, a weight, a gender, a height, a body mass index, a medical condition, a familial medication history, an injury, a medical procedure, a medication prescribed, or some combination thereof. The performance information may include, e.g., an elapsed time of using a treatment device, an amount of force exerted on a portion of the treatment device, a range of motion achieved on the treatment device, a movement speed of a portion of the treatment device, an indication of a plurality of pain levels using the treatment device, or some combination thereof. The measurement information may include, e.g., a vital sign, a respiration rate, a heartrate, a temperature, a blood pressure, or some combination thereof. It may be desirable to process the characteristics of a multitude of patients, the treatment plans performed for those patients, and the results of the treatment plans for those patients.

Doctors typically prescribe pain medication, such as opioids, to a patient after conducting a physical examination and/or communicating with the patient (e.g., to obtain the patient's rehabilitative progress and/or pain level). Another technical problem may involve distally treating, via a computing device during a telemedicine or telehealth session, a patient from a location different than a location at which the patient is located. An additional technical problem is controlling or enabling the control of, from the different location, a treatment device used by the patient at the location at which the patient is located. Oftentimes, when a patient undergoes rehabilitative surgery (e.g., knee surgery), a healthcare professional may prescribe a treatment device to the patient to use to perform a treatment protocol at their residence or any mobile location or temporary domicile. A healthcare professional may refer to a doctor, physician assistant, nurse, chiropractor, dentist, physical therapist, acupuncturist, physical trainer, coach, personal trainer, neurologist, cardiologist, or the like. A healthcare profession may refer to any person with a credential, license, degree, or the like in the field of medicine, physical therapy, rehabilitation, or the like.

When the healthcare professional is located in a location different from the patient and the treatment device, it may be technically challenging for the healthcare professional to monitor the patient's actual progress (as opposed to relying on the patient's word about the patient's progress) in using the treatment device, modify the treatment plan according to the patient's progress, adapt the treatment device to the personal characteristics of the patient as the patient performs the treatment plan, and the like.

Accordingly, systems and methods, such as those described herein, that use sensor data to modify a treatment plan and/or to adapt the treatment device while a patient performs the treatment plan using the treatment device, may be desirable.

In some embodiments, the systems and methods described herein may be configured to receive a treatment plan for a user, such as a patient. The treatment plan may correspond to a rehabilitation treatment plan, a prehabilitation treatment plan, an exercise treatment plan, or any other suitable treatment plan. The treatment plan may comprise one or more exercise routines for the patient to complete during one or more treatment sessions. The patient may include a person performing the one or more exercise routines. The person may perform the one or more exercise routines on a treatment device, such as a rehabilitation device. The system and methods may be configured to receive treatment data pertaining to the patient. The treatment data may include various characteristics of the patient, various measurement information pertaining to the patient while the patient uses the treatment device, various characteristics of the treatment device, the treatment plan, other suitable data, or a combination thereof. The system and methods may be configured to receive patient input correlating with at least one of the pain levels of the patient and use the treatment plan, the treatment data, and the patient input to generate at least one threshold. Responsive to an occurrence of exceeding the at least one threshold, the systems and methods can modify the treatment plan.

In some embodiments, while the patient uses the treatment device to perform the treatment plan, at least some of the treatment data may correspond to sensor data of a sensor configured to sense various characteristics of the treatment device and/or the measurement information of the patient. Additionally, or alternatively, while the patient uses the treatment device to perform the treatment plan, at least some of the treatment data may correspond to sensor data from a sensor associated with a wearable device configured to sense the measurement information of the patient.

The various characteristics of the treatment device may include one or more settings of the treatment device, a current revolutions per time period (e.g., such as one minute) of a rotating member (e.g., such as a wheel) of the treatment device, a resistance setting of the treatment device, other suitable characteristics of the treatment device, or a combination thereof. The measurement information may include one or more vital signs of the patient, a respiration rate of the patient, a heartrate of the patient, a temperature of the patient, a blood pressure of the patient, other suitable measurement information of the patient, or a combination thereof.

In some embodiments, the systems and methods described herein may be configured to generate treatment information using the treatment data. The treatment information may include a summary of the performance of the treatment plan by the patient while using the treatment device, such that the treatment data is presentable at a computing device of a healthcare professional responsible for the performance of the treatment plan by the patient. The healthcare professional may include a medical professional (e.g., such as a doctor, a nurse, a therapist, and the like), an exercise professional (e.g., such as a coach, a trainer, a nutritionist, and the like), or another professional sharing at least one of medical and exercise attributes (e.g., such as an exercise physiologist, a physical therapist, an occupational therapist, and the like). As used herein, and without limiting the foregoing, a "healthcare professional" may be a human being, a robot, a virtual assistant, a virtual assistant in a virtual and/or augmented reality, or an artificially intelligent entity, including a software program, integrated software and hardware, or hardware alone.

In some embodiments, the patient input may include a patient goal, a level of exhaustion, pain level, or any other suitable information or combination thereof. For example, the patient goal may include a target rehabilitation date, a maximum or a minimum length of time for one or more exercise sessions, a level of difficulty, or any other desired goal. The level of exhaustion may include the current level of exhaustion of the patient (e.g., based on a scale of pain level values from 1-10), the number of hours the patient slept during the previous night, or any other desired information. The pain level may include one or more levels of pain (e.g., based on a scale of pain level values from 1-10) the patient experiences before, during, and/or after the exercise sessions. The patient may input one or more pain level values correlating with one or more body parts. For example, a patient may be rehabilitating from a double knee surgery and each knee is recovering at different paces. The patient may be experiencing a pain level value of four on the right knee and a pain level value of seven on the left knee prior to an exercise session. The patient may experience an increase in pain levels during the exercise session (e.g., a pain level value of five on the right knee and a pain level value of nine on the left knee).

The threshold may include one or more threshold conditions. The one or more threshold conditions may be based on characteristics of the injury, the patient, the treatment plan, the recovery results, the examination results, the pain level, the level of exhaustion, the exercise session, any other suitable factors, or combination thereof. For example, a patient may be using a treatment device, such as an exercise bicycle, during a treatment session. The threshold may include a threshold condition that the patient cannot apply more than first and second amounts of measured force to right and left pedals, respectively. The treatment device may include one or more modes, such as an active-assisted mode, that can assist a user in cycling. The active-assisted mode may refer to a sensor of the treatment device receiving measurements of revolutions per minute of one or more radially-adjustable couplings, and causing the electric motor to drive the one or more radially-adjustable couplings rotationally coupled to the one or more pedals when the measured revolutions per minute satisfy a parameter (e.g., a threshold condition). The threshold condition may be configurable by the user and/or the physician, for example, as part of the treatment plan. The electric motor may be powered off while the user provides the driving force to the radially-adjustable couplings as long as the revolutions per minute are above a revolutions per minute threshold and the threshold condition is not satisfied. When the revolutions per minute are less than the revolutions per minute threshold then the threshold condition is satisfied and the electric motor may be controlled to drive the radially-adjustable couplings to maintain the revolutions per minute threshold.

Responsive to an occurrence of exceeding the at least one threshold, the artificial intelligence engine may be trained to modify the treatment plan. Modifying the treatment plan may comprise generating at least one updated exercise routine during one of the one or more treatment sessions. For example, if the patient's pain level exceeds a threshold during a treatment session, the artificial intelligence engine may generate an updated exercise routine. The updated exercise routine may include changes, such as changes to an amount of time of the treatment session, an amount of time between treatment sessions (e.g., for the patient to rest and for the patient's pain level to decrease), a type of exercise to be completed in the treatment session, a type of treatment device for the patient to perform on during the treatment session, any other desired modification, or combination thereof. The updated exercise routine may include a changes to parameters of the treatment device, such as changes to a radius of one or more of the pedals, a level of assistance applied by the electric motor to assist the patient with cycling, an amount of resistance the electric motor applies to the one or more pedals, any other desired change to a parameter, or combination thereof.

In some embodiments, the systems and methods can control the treatment device while the patient uses the treatment device, including during a telemedicine session. The controlling can be based on parameters of the modified treatment plan. For example, the artificial intelligence engine may be configured to modify the treatment plan such that the treatment device changes a radius of rotation of one or more of the pedals, a level of assistance applied by the electric motor to assist the patient with cycling, an amount of resistance the electric motor applies to the one or more pedals, any other desired control, or combination thereof.

In some embodiments, the artificial intelligence engine can be configured to receive the modified patient input correlating with an updated pain level of the patient (e.g., the patient inputs a change in pain level during a treatment session) and use the modified treatment plan, the treatment data, and the modified patient input to generate at least one modified threshold. Responsive to an occurrence of exceeding the at least one modified threshold, the artificial intelligence engine can be configured to modify the modified treatment plan. The modified treatment plan can include one or more modifications that differ from the treatment plan. For example, the modified treatment plan may differ from the treatment plan by having one or more different exercise routines for the patient to perform on a treatment device, one or more different parameters for controlling the treatment device, one or more different thresholds, any other differences, or combinations thereof.

In some embodiments, at least one of the treatment data and the patient input can be received in real-time or near real-time and the treatment plan can be modified in real-time or near real-time. The In some embodiments, at least one of the modified patient input and the modified patient input can be received in real-time or near real-time and the modified treatment plan can be modified in real-time or near real-time.

In some embodiments, the healthcare professional may review the treatment information and determine whether to modify the treatment plan and/or one or more characteristics of the treatment device. For example, the healthcare professional may review the treatment information and compare the treatment information to the treatment plan being performed by the patient.

Depending on what result is desired, the artificial intelligence engine may be trained to output several treatment plans. For example, one result may include recovering to a threshold level (e.g., 75% range of motion) in a fastest amount of time, while another result may include fully recovering (e.g., 100% range of motion) regardless of the amount of time. Another result may include recovering while not exceeding a threshold level for pain (e.g., at or below a specific pain level) between treatment sessions, while another result may include recovering while not exceeding a threshold level for pain during a treatment session.

The artificial intelligence engine may compare the following (i) expected information, which pertains to the patient while the patient uses the treatment device to perform the treatment plan to (ii) the measurement information (e.g., indicated by the treatment information), which pertains to the patient while the patient uses the treatment device to perform the treatment plan. The expected information may include one or more vital signs of the patient, a respiration rate of the patient, a heartrate of the patient, a temperature of the patient, a blood pressure of the patient, other suitable information of the patient, or a combination thereof. The artificial intelligence engine may determine that the treatment plan is optimal for the particular patient (i.e., the patient is having a desired rehabilitation result) if one or more parts or portions of the measurement information are within an acceptable range associated with one or more corresponding parts or portions of the expected information (e.g., within one or more thresholds). Conversely, the artificial intelligence engine may determine that the treatment plan is not optimal for the particular patient (i.e., the patient is not having a desired rehabilitation result) if one or more parts or portions of the measurement information are outside of the range associated with one or more corresponding parts or portions of the expected information (e.g., outside of the one or more thresholds).

For example, the artificial intelligence engine may determine whether a blood pressure value (e.g., systolic pressure, diastolic pressure, and/or pulse pressure) corresponding to the patient while the patient uses the treatment device (e.g., indicated by the measurement information) is within an acceptable range (e.g., plus or minus 1%, plus or minus 5%, or any suitable range) of an expected blood pressure value indicated by the expected information. The artificial intelligence engine may determine that the treatment plan is having the desired effect if the blood pressure value corresponding to the patient while the patient uses the treatment device is within the range of the expected blood pressure value. Conversely, the artificial intelligence engine may determine that the treatment plan is not having the desired effect if the blood pressure value corresponding to the patient while the patient uses the treatment device is outside of the range of the expected blood pressure value.

In another example, the artificial intelligence engine may determine whether a pain level corresponding to the patient while the patient uses the treatment device (e.g., indicated by the patient input) is within an acceptable range of an expected pain level value indicated by the expected information (e.g., a pain level value for a patient two days after surgery is expected to be higher than the pain level value of the patient two weeks after the surgery, a pain level value for a patient having right ankle surgery is expected to be higher during recovery than an uninjured left ankle). The artificial intelligence engine may determine that the treatment plan is having the desired effect if the pain level corresponding to the patient while the patient uses the treatment device is within the range of the expected pain level value (e.g., not exceeding the threshold). Conversely, the artificial intelligence engine may determine that the treatment plan is not having the desired effect if the pain level value corresponding to the patient while the patient uses the treatment device is outside of the range of the expected pain level value. If the artificial intelligence engine determines that an occurrence of exceeding the at least one threshold occurs, then the artificial intelligence engine may be configured to modify the treatment plan or any previously modified treatment plans.

In some embodiments, the artificial intelligence engine may compare the expected characteristics of the treatment device while the patient uses the treatment device to perform the treatment plan with characteristics of the treatment device indicated by the treatment information. For example, the artificial intelligence engine may compare an expected resistance setting of the treatment device with an actual resistance setting of the treatment device indicated by the treatment information. The artificial intelligence engine may determine that the user is performing the treatment plan properly if the actual characteristics of the treatment device indicated by the treatment information are within a range of corresponding ones of the expected characteristics of the treatment device. Conversely, the artificial intelligence engine may determine that the user is not performing the treatment plan properly if the actual characteristics of the treatment device indicated by the treatment information are outside the range of corresponding ones of the expected characteristics of the treatment device. If the artificial intelligence engine determines that an occurrence of exceeding the at least one threshold occurs, then the artificial intelligence engine may be configured to modify the treatment plan or any previously modified treatment plans.

If the artificial intelligence engine determines that the treatment information indicates that the user is performing the treatment plan properly and/or that the treatment plan is having the desired effect, the artificial intelligence engine may determine not to modify the treatment plan or the one or more characteristics of the treatment device. Conversely, while the patient uses the treatment device to perform the treatment plan, if the artificial intelligence engine determines that the treatment information indicates that the patient is not or has not been performing the treatment plan properly and/or that the treatment plan is not or has not been having the desired effect, the artificial intelligence engine may determine to modify the treatment plan and/or the one or more characteristics of the treatment device.

In some embodiments, the system may interact with a user interface to provide treatment plan input indicating one or more modifications to the treatment plan and/or to one or more characteristics of the treatment device if the artificial intelligence engine determines to modify the treatment plan and/or the one or more characteristics of the treatment device. For example, the interface may provide input indicating an increase or decrease in the resistance setting of the treatment device, an increase or decrease in an amount of time the user is required to use the treatment device according to the treatment plan, or other suitable modification to the one or more characteristics of the treatment device.

In some embodiments, the systems and methods described herein may be configured to modify the treatment plan based on one or more modifications indicated by the treatment plan input. Additionally, or alternatively, the systems and methods described herein may be configured to modify the one or more characteristics of the treatment device based on the modified treatment plan and/or the treatment plan input. For example, the treatment plan input may indicate to modify the one or more characteristics of the treatment device and/or the modified treatment plan may require or indicate adjustments to the treatment device in order for the user to achieve the desired results of the modified treatment plan.

In some embodiments, the systems and methods described herein may be configured to receive subsequent treatment data pertaining to the user while the user uses the treatment device to perform the modified treatment plan. For example, after the artificial intelligence engine modifies the treatment plan and/or controls the one or more characteristics of the treatment device, the user may continue use the treatment device to perform the modified treatment plan. The subsequent treatment data may correspond to treatment data generated while the user uses the treatment device to perform the modified treatment plan. In some embodiments, the subsequent treatment data may correspond to treatment data generated while the user continues to use the treatment device to perform the treatment plan, after the healthcare professional has received the treatment information and determined not to modify the treatment plan and/or control the one or more characteristics of the treatment device.

Based on subsequent (e.g., modified) treatment plan input generated by the artificial intelligence engine, the systems and methods described herein may be configured to further modify the treatment plan and/or control the one or more characteristics of the treatment device. The subsequent treatment plan input may correspond to input provided by the patient at the user interface, from treatment data corresponding to sensor data from a sensor of a wearable device worn by the patient during one of the one or more treatment sessions, from a sensor configured to detect treatment data pertaining to the patient, any other desired information, or combination thereof.

The healthcare professional may receive and/or review treatment information continuously or periodically while the user uses the treatment device to perform the treatment plan. Based on one or more trends indicated by the continuously and/or periodically received treatment information, the healthcare professional may determine whether to modify the treatment plan and/or control the one or more characteristics of the treatment device. For example, the one or more trends may indicate an increase in heart rate or other suitable trends indicating that the user is not performing the treatment plan properly and/or performance of the treatment plan by the person is not having the desired effect.

In some embodiments, the systems and methods described herein may be configured to use artificial intelligence and/or machine learning to assign patients to cohorts and to dynamically control a treatment device based on the assignment during an adaptive telemedicine session. In some embodiments, numerous treatment devices may be provided to patients. The treatment devices may be used by the patients to perform treatment plans in their residences, at a gym, at a rehabilitative center, at a hospital, or any suitable location, including permanent or temporary domiciles.

In some embodiments, the treatment devices may be communicatively coupled to a server. Characteristics of the patients, including the treatment data, may be collected before, during, and/or after the patients perform the treatment plans. For example, the personal information, the performance information, and the measurement information may be collected before, during, and/or after the patient performs the treatment plans. The results (e.g., improved performance or decreased performance) of performing each exercise may be collected from the treatment device throughout the treatment plan and after the treatment plan is performed. The parameters, settings, configurations, etc. (e.g., position of pedal, amount of resistance, etc.) of the treatment device may be collected before, during, and/or after the treatment plan is performed.

Each characteristic of the patient, each result, and each parameter, setting, configuration, etc. may be timestamped and may be correlated with a particular step in the treatment plan. Such a technique may enable determining which steps in the treatment plan lead to desired results (e.g., improved muscle strength, range of motion, etc.) and which steps lead to diminishing returns (e.g., continuing to exercise after 3 minutes actually delays or harms recovery).

Data may be collected from the treatment devices and/or any suitable computing device (e.g., computing devices where personal information is entered, such as the interface of the computing device described herein, a clinician interface, patient interface, and the like) over time as the patients use the treatment devices to perform the various treatment plans. The data that may be collected may include the characteristics of the patients, the treatment plans performed by the patients, the results of the treatment plans, any of the data described herein, any other suitable data, or a combination thereof.

In some embodiments, the data may be processed to group certain patients into cohorts. The patients may be grouped by patients having certain or selected similar characteristics, treatment plans, and results of performing the treatment plans. For example, athletic patients having no medical conditions who perform a treatment plan (e.g., use the treatment device for 30 minutes a day 5 times a week for 3 weeks) and who fully recover may be grouped into a first cohort. Older patients who are classified obese and who perform a treatment plan (e.g., use the treatment plan for 10 minutes a day 3 times a week for 4 weeks) and who improve their range of motion by 75 percent may be grouped into a second cohort.

In some embodiments, an artificial intelligence engine may include one or more machine learning models that are trained using the cohorts. For example, the one or more machine learning models may be trained to receive an input of characteristics of a new patient and to output a treatment plan for the patient that results in a desired result. The machine learning models may match a pattern between the characteristics of the new patient and at least one patient of the patients included in a particular cohort. When a pattern is matched, the machine learning models may assign the new patient to the particular cohort and select the treatment plan associated with the at least one patient. The artificial intelligence engine may be configured to control, distally and based on the treatment plan, the treatment device while the new patient uses the treatment device to perform the treatment plan.

As may be appreciated, the characteristics of the new patient (e.g., a new user) may change as the new patient uses the treatment device to perform the treatment plan. For example, the performance of the patient may improve quicker than expected for patients in the cohort to which the new patient is currently assigned. Accordingly, the machine learning models may be trained to dynamically reassign, based on the changed characteristics, the new patient to a different cohort that includes patients having characteristics similar to the now-changed characteristics as the new patient. For example, a clinically obese patient may lose weight and no longer meet the weight criterion for the initial cohort, result in the patient's being reassigned to a different cohort with a different weight criterion.

A different treatment plan may be selected for the new patient, and the treatment device may be controlled, distally (e.g., which may be referred to as remotely) and based on the different treatment plan, the treatment device while the new patient uses the treatment device to perform the treatment plan. Such techniques may provide the technical solution of distally controlling a treatment device.

Further, the systems and methods described herein may lead to faster recovery times and/or better results for the patients because the treatment plan that most accurately fits their characteristics is selected and implemented, in real-time, at any given moment. "Real-time" may also refer to near real-time, which may be less than 10 seconds or any reasonably proximate difference between two times. As described herein, the term "results" may refer to medical results or medical outcomes. Results and outcomes may refer to responses to medical actions. The term "medical action(s)" may refer to any suitable action(s) performed by the healthcare professional, and such action or actions may include diagnoses, prescriptions for treatment plans, prescriptions for treatment devices, and the making, composing and/or executing of appointments, telemedicine sessions, prescription of medicines, telephone calls, emails, text messages, and the like.

Further, the artificial intelligence engine may be trained to output treatment plans that are not optimal i.e., sub-optimal, nonstandard, or otherwise excluded (all referred to, without limitation, as "excluded treatment plans") for the patient. For example, if a patient has high blood pressure, a particular exercise may not be approved or suitable for the patient as it may put the patient at unnecessary risk or even induce a hypertensive crisis and, accordingly, that exercise may be flagged in the excluded treatment plan for the patient. In some embodiments, the artificial intelligence engine may monitor the treatment data received while the patient (e.g., the user) with, for example, high blood pressure, uses the treatment device to perform an appropriate treatment plan and may modify the appropriate treatment plan to include features of an excluded treatment plan that may provide beneficial results for the patient if the treatment data indicates the patient is handling the appropriate treatment plan without aggravating, for example, the high blood pressure condition of the patient.

In some embodiments, the treatment plans and/or excluded treatment plans may be presented, during a telemedicine or telehealth session, to a healthcare professional. The healthcare professional may select a particular treatment plan for the patient to cause that treatment plan to be transmitted to the patient and/or to control, based on the treatment plan, the treatment device. In some embodiments, to facilitate telehealth or telemedicine applications, including remote diagnoses, determination of treatment plans and rehabilitative and/or pharmacologic prescriptions, the artificial intelligence engine may receive and/or operate distally from the patient and the treatment device.

In such cases, the recommended treatment plans and/or excluded treatment plans may be presented simultaneously with a video of the patient in real-time or near real-time during a telemedicine or telehealth session on a user interface of a computing device of a healthcare professional. The video may also be accompanied by audio, text and other multimedia information and/or sensorial or perceptive (e.g., tactile, gustatory, haptic, pressure-sensing-based or electromagnetic (e.g., neurostimulation)). Real-time may refer to less than or equal to 2 seconds. Near real-time may refer to any interaction of a sufficiently short time to enable two individuals to engage in a dialogue via such user interface, and will generally be less than 10 seconds (or any suitable proximate difference between two different times) but greater than 2 seconds.

Presenting the treatment plans generated by the artificial intelligence engine concurrently with a presentation of the patient video may provide an enhanced user interface because the healthcare professional may continue to visually and/or otherwise communicate with the patient while also reviewing the treatment plans on the same user interface. The enhanced user interface may improve the healthcare professional's experience using the computing device and may encourage the healthcare professional to reuse the user interface. Such a technique may also reduce computing resources (e.g., processing, memory, network) because the healthcare professional does not have to switch to another user interface screen to enter a query for a treatment plan to recommend based on the characteristics of the patient. The artificial intelligence engine may be configured to provide, dynamically on the fly, the treatment plans and excluded treatment plans.

In some embodiments, the treatment device may be adaptive and/or personalized because its properties, configurations, and positions may be adapted to the needs of a particular patient. For example, the pedals may be dynamically adjusted on the fly (e.g., via a telemedicine session or based on programmed configurations in response to certain measurements being detected) to increase or decrease a range of motion to comply with a treatment plan designed for the user. In some embodiments, a healthcare professional may adapt, remotely during a telemedicine session, the treatment device to the needs of the patient by causing a control instruction to be transmitted from a server to treatment device. Such adaptive nature may improve the results of recovery for a patient, furthering the goals of personalized medicine, and enabling personalization of the treatment plan on a per-individual basis.

FIG. 1 shows a block diagram of a computer-implemented system 10, hereinafter called "the system" for managing a treatment plan. Managing the treatment plan may include using an artificial intelligence engine to recommend treatment plans and/or provide excluded treatment plans that should not be recommended to a patient.

The system 10 also includes a server 30 configured to store and to provide data related to managing the treatment plan. The server 30 may include one or more computers and may take the form of a distributed and/or virtualized computer or computers. The server 30 may also include a first communication interface 32 configured to communicate with the clinician interface 20 via a first network 34. In some embodiments, the first network 34 may include wired and/or wireless network connections such as Wi-Fi, Bluetooth, ZigBee, Near-Field Communications (NFC), cellular data networks, etc. The server 30 may include a first processor 36 and a first machine-readable storage memory 38 (the latter of which may be called a "memory" for short), holding first instructions 40 for performing the various actions of the server 30 for execution by the first processor 36. The server 30 may be configured to store data regarding the treatment plan. For example, the memory 38 includes a system data store 42 configured to hold system data, such as data pertaining to treatment plans for treating one or more patients. The server 30 may also be configured to store data regarding performance by a patient in following a treatment plan. For example, the memory 38 includes a patient data store 44 configured to hold patient data, such as data pertaining to the one or more patients, including data representing each patient's performance within the treatment plan.

In addition, the characteristics (e.g., personal, performance, measurement, etc.) of the patients, the treatment plans followed by the patients, the level of compliance with the treatment plans, and the results of the treatment plans may use correlations and other statistical or probabilistic measures to enable the partitioning of or to partition the treatment plans into different patient cohort-equivalent databases in the patient data store 44. For example, the data for a first cohort of first patients having a first similar injury, a first similar medical condition, a first similar medical procedure performed, a first treatment plan followed by the first patient, and a first result of the treatment plan may be stored in a first patient database. The data for a second cohort of second patients having a second similar injury, a second similar medical condition, a second similar medical procedure performed, a second treatment plan followed by the second patient, and a second result of the treatment plan may be stored in a second patient database. Any single characteristic or any combination of characteristics may be used to separate the cohorts of patients. In some embodiments, the different cohorts of patients may be stored in different partitions or volumes of the same database. There is no specific limit to the number of different cohorts of patients allowed, other than as limited by mathematical combinatoric and/or partition theory.

This characteristic data, treatment plan data, and results data may be obtained from numerous treatment apparatuses and/or computing devices over time and stored in the database 44. The characteristic data, treatment plan data, and results data may be correlated in the patient-cohort databases in the patient data store 44. The characteristics of the patients may include personal information, performance information, and/or measurement information.

In addition to the historical information about other patients stored in the patient cohort-equivalent databases, real-time or near-real-time information based on the current patient's characteristics about a current patient being treated may be stored in an appropriate patient cohort-equivalent database. The characteristics of the patient may be determined to match or be similar to the characteristics of another patient in a particular cohort (e.g., cohort A) and the patient may be assigned to that cohort.

In some embodiments, the server 30 may execute an artificial intelligence (AI) engine 11 that uses one or more machine learning models 13 to perform at least one of the embodiments disclosed herein. The server 30 may include a training engine 9 capable of generating the one or more machine learning models 13. The machine learning models 13 may be trained to assign patients to certain cohorts based on their characteristics, select treatment plans using real-time and historical data correlations involving patient cohort-equivalents, and control a treatment apparatus 70, among other things. The one or more machine learning models 13 may be generated by the training engine 9 and may be implemented in computer instructions executable by one or more processing devices of the training engine 9 and/or the servers 30. To generate the one or more machine learning models 13, the training engine 9 may train the one or more machine learning models 13. The one or more machine learning models 13 may be used by the artificial intelligence engine 11.

The training engine 9 may be a rackmount server, a router computer, a personal computer, a portable digital assistant, a smartphone, a laptop computer, a tablet computer, a netbook, a desktop computer, an Internet of Things (IoT) device, any other desired computing device, or any combination of the above. The training engine 9 may be cloud-based, a real-time software platform, or an embedded system (e.g., microcode-based and/or implemented) and it may include privacy software or protocols, and/or security software or protocols.

To train the one or more machine learning models 13, the training engine 9 may use a training data set of a corpus of the characteristics of the patients that used the treatment apparatus 70 to perform treatment plans, the details (e.g., treatment protocol including exercises, amount of time to perform the exercises, how often to perform the exercises, a schedule of exercises, parameters/configurations/settings of the treatment apparatus 70 throughout each step of the treatment plan, etc.) of the treatment plans performed by the patients using the treatment apparatus 70, and the results of the treatment plans performed by the patients. The one or more machine learning models 13 may be trained to match patterns of characteristics of a patient with characteristics of other patients in assigned to a particular cohort. The term "match" may refer to an exact match, a correlative match, a substantial match, etc. The one or more machine learning models 13 may be trained to receive the characteristics of a patient as input, map the characteristics to characteristics of patients assigned to a cohort, and select a treatment plan from that cohort. The one or more machine learning models 13 may also be trained to control, based on the treatment plan, the treatment apparatus 70.

Different machine learning models 13 may be trained to recommend different treatment plans for different desired results. For example, one machine learning model may be trained to recommend treatment plans for most effective recovery, while another machine learning model may be trained to recommend treatment plans based on speed of recovery.

Using training data that includes training inputs and corresponding target outputs, the one or more machine learning models 13 may refer to model artifacts created by the training engine 9. The training engine 9 may find patterns in the training data wherein such patterns map the training input to the target output, and generate the machine learning models 13 that capture these patterns. In some embodiments, the artificial intelligence engine 11, the database 33, and/or the training engine 9 may reside on another component (e.g., assistant interface 94, clinician interface 20, etc.) depicted in FIG. 1.

The one or more machine learning models 13 may comprise, e.g., a single level of linear or non-linear operations (e.g., a support vector machine [SVM]) or the machine learning models 13 may be a deep network, i.e., a machine learning model comprising multiple levels of non-linear operations. Examples of deep networks are neural networks including generative adversarial networks, convolutional neural networks, recurrent neural networks with one or more hidden layers, and fully connected neural networks (e.g., each neuron may transmit its output signal to the input of the remaining neurons, as well as to itself). For example, the machine learning model may include numerous layers and/or hidden layers that perform calculations (e.g., dot products) using various neurons.

The system 10 also includes a patient interface 50 configured to communicate information to a patient and to receive feedback from the patient. Specifically, the patient interface includes an input device 52 and an output device 54, which may be collectively called a patient user interface 52, 54. The input device 52 may include one or more devices, such as a keyboard, a mouse, a touch screen input, a gesture sensor, and/or a microphone and processor configured for voice recognition. The output device 54 may take one or more different forms including, for example, a computer monitor or display screen on a tablet, smartphone, or a smart watch. The output device 54 may include other hardware and/or software components such as a projector, virtual reality capability, augmented reality capability, etc. The output device 54 may incorporate various different visual, audio, or other presentation technologies. For example, the output device 54 may include a non-visual display, such as an audio signal, which may include spoken language and/or other sounds such as tones, chimes, and/or melodies, which may signal different conditions and/or directions. The output device 54 may comprise one or more different display screens presenting various data and/or interfaces or controls for use by the patient. The output device 54 may include graphics, which may be presented by a web-based interface and/or by a computer program or application (App.).

As shown in FIG. 1, the patient interface 50 includes a second communication interface 56 (one example of an "input device", an "output device," or both), which may also be called a remote communication interface configured to communicate with the server 30 and/or the clinician interface 20 via a second network 58. In some embodiments, the second network 58 may include a local area network (LAN), such as an Ethernet network. In some embodiments, the second network 58 may include the Internet, and communications between the patient interface 50 and the server 30 and/or the clinician interface 20 may be secured via encryption, such as, for example, by using a virtual private network (VPN). In some embodiments, the second network 58 may include wired and/or wireless network connections such as Wi-Fi, Bluetooth, ZigBee, Near-Field Communications (NFC), cellular data networks, etc. In some embodiments, the second network 58 may be the same as and/or operationally coupled to the first network 34.

The patient interface 50 may include a second processor 60 and a second machine-readable storage memory 62 holding second instructions 64 for execution by the second processor 60 for performing various actions of patient interface 50. The second machine-readable storage memory 62 also includes a local data store 66 configured to hold data, such as data pertaining to a treatment plan and/or patient data, such as data representing a patient's performance within a treatment plan. The patient interface 50 also includes a local communication interface 68 configured to communicate with various devices for use by the patient in the vicinity of the patient interface 50. The local communication interface 68 (one example of an "input device," an "output device," or both) may include wired and/or wireless communications. In some embodiments, the local communication interface 68 may include a local wireless network such as Wi-Fi, Bluetooth, ZigBee, Near-Field Communications (NFC), cellular data networks, etc.

The system 10 also includes a treatment apparatus 70 configured to be manipulated by the patient and/or to manipulate a body part of the patient for performing activities according to the treatment plan. In some embodiments, the treatment apparatus 70 may take the form of an exercise and rehabilitation apparatus configured to perform and/or to aid in the performance of a rehabilitation regimen, which may be an orthopedic rehabilitation regimen, and the treatment includes rehabilitation of a body part of the patient, such as a joint or a bone or a muscle group. The treatment apparatus 70 (one example of a "treatment device") may be any suitable medical, rehabilitative, therapeutic, etc. apparatus configured to be controlled distally via another computing device to treat a patient and/or exercise the patient. The treatment apparatus 70 may be an electromechanical machine including one or more weights, an electromechanical bicycle, an electromechanical spin-wheel, a smart-mirror, a treadmill, or the like. The body part may include, for example, a spine, a hand, a foot, a knee, or a shoulder. The body part may include a part of a joint, a bone, or a muscle group, such as one or more vertebrae, a tendon, or a ligament. As shown in FIG. 1, the treatment apparatus 70 includes a controller 72, which may include one or more processors, computer memory, and/or other components. The treatment apparatus 70 may also include a fourth communication interface 74 configured to communicate with the patient interface 50 via the local communication interface 68. The treatment apparatus 70 may also include one or more internal sensors 76 and an actuator 78, such as a motor. The actuator 78 may be used, for example, for moving the patient's body part and/or for resisting forces by the patient.

The internal sensors 76 may measure one or more operating characteristics of the treatment apparatus 70 such as, for example, a force, a position, a speed, and/or a velocity. In some embodiments, the internal sensors 76 may include a position sensor configured to measure at least one of a linear motion or an angular motion of a body part of the patient. For example, an internal sensor 76 in the form of a position sensor may measure a distance that the patient is able to move a part of the treatment apparatus 70, where such distance may correspond to or translate into a range of motion that the patient's body part is able to achieve. In some embodiments, the internal sensors 76 may include a force sensor configured to measure a force applied by the patient. For example, an internal sensor 76 in the form of a force sensor may measure a force or weight the patient, using a particular body part, is able to apply to the treatment apparatus 70.

The system 10 shown in FIG. 1 also includes an ambulation sensor 82, which communicates with the server 30 via the local communication interface 68 of the patient interface 50. The ambulation sensor 82 may track and store a number of steps taken by the patient. In some embodiments, the ambulation sensor 82 may take the form of a wristband, wristwatch, or smart watch. In some embodiments, the ambulation sensor 82 may be integrated within a phone, such as a smartphone.

The system 10 shown in FIG. 1 also includes a goniometer 84, which communicates with the server 30 via the local communication interface 68 of the patient interface 50. The goniometer 84 measures an angle of the patient's body part. For example, the goniometer 84 may measure the angle of flex of a patient's knee or elbow or shoulder.

The system 10 shown in FIG. 1 also includes a pressure sensor 86, which communicates with the server 30 via the local communication interface 68 of the patient interface 50. The pressure sensor 86 measures an amount of pressure or weight applied by a body part of the patient. For example, pressure sensor 86 may measure an amount of force applied by a patient's foot when pedaling a stationary bike The system 10 shown in FIG. 1 also includes a supervisory interface 90 which may be similar or identical to the clinician interface 20. In some embodiments, the supervisory interface 90 may have enhanced functionality beyond what is provided on the clinician interface 20. The supervisory interface 90 may be configured for use by a person having responsibility for the treatment plan, such as an orthopedic surgeon.

The system 10 shown in FIG. 1 also includes a reporting interface 92 which may be similar or identical to the clinician interface 20. In some embodiments, the reporting interface 92 may have less functionality than the clinician interface 20. For example, the reporting interface 92 may not have the ability to modify a treatment plan. Such a reporting interface 92 may be used, for example, by a biller to determine the use of the system 10 for billing purposes. In another example, the reporting interface 92 may not have the ability to display patient identifiable information, presenting only pseudonymized data and/or anonymized data for certain data fields concerning a data subject and/or for certain data fields concerning a quasi-identifier of the data subject. Such a reporting interface 92 may be used, for example, by a researcher to determine various effects of a treatment plan on different patients.

The system 10 includes an assistant interface 94 for an assistant, such as a doctor, a nurse, a physical therapist, a technician, or a healthcare professional, to remotely communicate with the patient interface 50 and/or the treatment apparatus 70. Such remote communications may enable the assistant to provide assistance or guidance to a patient using the system 10. More specifically, the assistant interface 94 is configured to communicate a telemedicine signal 96, 97, 98a, 98b, 99a, 99b with the patient interface 50 via a network connection such as, for example, via the first network 34 and/or the second network 58. The telemedicine signal 96, 97, 98a, 98b, 99a, 99b comprises one of an audio signal 96, an audiovisual signal 97, an interface control signal 98a for controlling a function of the patient interface 50, an interface monitor signal 98b for monitoring a status of the patient interface 50, an apparatus control signal 99a for changing an operating parameter of the treatment apparatus 70, and/or an apparatus monitor signal 99b for monitoring a status of the treatment apparatus 70. In some embodiments, each of the control signals 98a, 99a may be unidirectional, conveying commands from the assistant interface 94 to the patient interface 50. In some embodiments, in response to successfully receiving a control signal 98a, 99a and/or to communicate successful and/or unsuccessful implementation of the requested control action, an acknowledgement message may be sent from the patient interface 50 to the assistant interface 94. In some embodiments, each of the monitor signals 98b, 99b may be unidirectional, status-information commands from the patient interface 50 to the assistant interface 94. In some embodiments, an acknowledgement message may be sent from the assistant interface 94 to the patient interface 50 in response to successfully receiving one of the monitor signals 98b, 99b.

In some embodiments, the patient interface 50 may be configured as a pass-through for the apparatus control signals 99a and the apparatus monitor signals 99b between the treatment apparatus 70 and one or more other devices, such as the assistant interface 94 and/or the server 30. For example, the patient interface 50 may be configured to transmit an apparatus control signal 99a in response to an apparatus control signal 99a within the telemedicine signal 96, 97, 98a, 98b, 99a, 99b from the assistant interface 94.

In some embodiments, the assistant interface 94 may be presented on a shared physical device as the clinician interface 20. For example, the clinician interface 20 may include one or more screens that implement the assistant interface 94. Alternatively or additionally, the clinician interface 20 may include additional hardware components, such as a video camera, a speaker, and/or a microphone, to implement aspects of the assistant interface 94.

In some embodiments, one or more portions of the telemedicine signal 96, 97, 98a, 98b, 99a, 99b may be generated from a prerecorded source (e.g., an audio recording, a video recording, or an animation) for presentation by the output device 54 of the patient interface 50. For example, a tutorial video may be streamed from the server 30 and presented upon the patient interface 50. Content from the prerecorded source may be requested by the patient via the patient interface 50. Alternatively, via a control on the assistant interface 94, the assistant may cause content from the prerecorded source to be played on the patient interface 50.

The assistant interface 94 includes an assistant input device 22 and an assistant display 24, which may be collectively called an assistant user interface 22, 24. The assistant input device 22 may include one or more of a telephone, a keyboard, a mouse, a trackpad, or a touch screen, for example. Alternatively or additionally, the assistant input device 22 may include one or more microphones. In some embodiments, the one or more microphones may take the form of a telephone handset, headset, or wide-area microphone or microphones configured for the assistant to speak to a patient via the patient interface 50. In some embodiments, assistant input device 22 may be configured to provide voice-based functionalities, with hardware and/or software configured to interpret spoken instructions by the assistant by using the one or more microphones. The assistant input device 22 may include functionality provided by or similar to existing voice-based assistants such as Siri by Apple, Alexa by Amazon, Google Assistant, or Bixby by Samsung. The assistant input device 22 may include other hardware and/or software components. The assistant input device 22 may include one or more general purpose devices and/or special-purpose devices.

The assistant display 24 may take one or more different forms including, for example, a computer monitor or display screen on a tablet, a smartphone, or a smart watch. The assistant display 24 may include other hardware and/or software components such as projectors, virtual reality capabilities, or augmented reality capabilities, etc. The assistant display 24 may incorporate various different visual, audio, or other presentation technologies. For example, the assistant display 24 may include a non-visual display, such as an audio signal, which may include spoken language and/or other sounds such as tones, chimes, melodies, and/or compositions, which may signal different conditions and/or directions. The assistant display 24 may comprise one or more different display screens presenting various data and/or interfaces or controls for use by the assistant. The assistant display 24 may include graphics, which may be presented by a web-based interface and/or by a computer program or application (App.).

In some embodiments, the system 10 may provide computer translation of language from the assistant interface 94 to the patient interface 50 and/or vice-versa. The computer translation of language may include computer translation of spoken language and/or computer translation of text, wherein the text and/or spoken language may be any language, formal or informal, current or outdated, digital, quantum or analog, invented, human or animal (e.g., dolphin) or ancient, with respect to the foregoing, e.g., Old English, Zulu, French, Japanese, Klingon, Kobaïan, Attic Greek, Modern Greek, etc., and in any form, e.g., academic, dialectical, patois, informal, e.g., "electronic texting," etc. Additionally or alternatively, the system 10 may provide voice recognition and/or spoken pronunciation of text. For example, the system 10 may convert spoken words to printed text and/or the system 10 may audibly speak language from printed text. The system 10 may be configured to recognize spoken words by any or all of the patient, the clinician, and/or the assistant. In some embodiments, the system 10 may be configured to recognize and react to spoken requests or commands by the patient. For example, the system 10 may automatically initiate a telemedicine session in response to a verbal command by the patient (which may be given in any one of several different languages).

In some embodiments, the server 30 may generate aspects of the assistant display 24 for presentation by the assistant interface 94. For example, the server 30 may include a web server configured to generate the display screens for presentation upon the assistant display 24. For example, the artificial intelligence engine 11 may generate recommended treatment plans and/or excluded treatment plans for patients and generate the display screens including those recommended treatment plans and/or external treatment plans for presentation on the assistant display 24 of the assistant interface 94. In some embodiments, the assistant display 24 may be configured to present a virtualized desktop hosted by the server 30. In some embodiments, the server 30 may be configured to communicate with the assistant interface 94 via the first network 34. In some embodiments, the first network 34 may include a local area network (LAN), such as an Ethernet network. In some embodiments, the first network 34 may include the Internet, and communications between the server 30 and the assistant interface 94 may be secured via privacy enhancing technologies, such as, for example, by using encryption over a virtual private network (VPN). Alternatively or additionally, the server 30 may be configured to communicate with the assistant interface 94 via one or more networks independent of the first network 34 and/or other communication means, such as a direct wired or wireless communication channel. In some embodiments, the patient interface 50 and the treatment apparatus 70 may each operate from a patient location geographically separate from a location of the assistant interface 94. For example, the patient interface 50 and the treatment apparatus 70 may be used as part of an in-home rehabilitation system, which may be aided remotely by using the assistant interface 94 at a centralized location, such as a clinic or a call center.

In some embodiments, the assistant interface 94 may be one of several different terminals (e.g., computing devices) that may be physically, virtually or electronically grouped together, for example, in one or more call centers or at one or more clinicians' offices. In some embodiments, a plurality of assistant interfaces 94 may be distributed geographically. In some embodiments, a person may work as an assistant remotely from any conventional office infrastructure, including a home office. Such remote work may be performed, for example, where the assistant interface 94 takes the form of a computer and/or telephone. This remote work functionality may allow for work-from-home arrangements that may include full-time, part-time and/or flexible work hours for an assistant.

Figure 2:
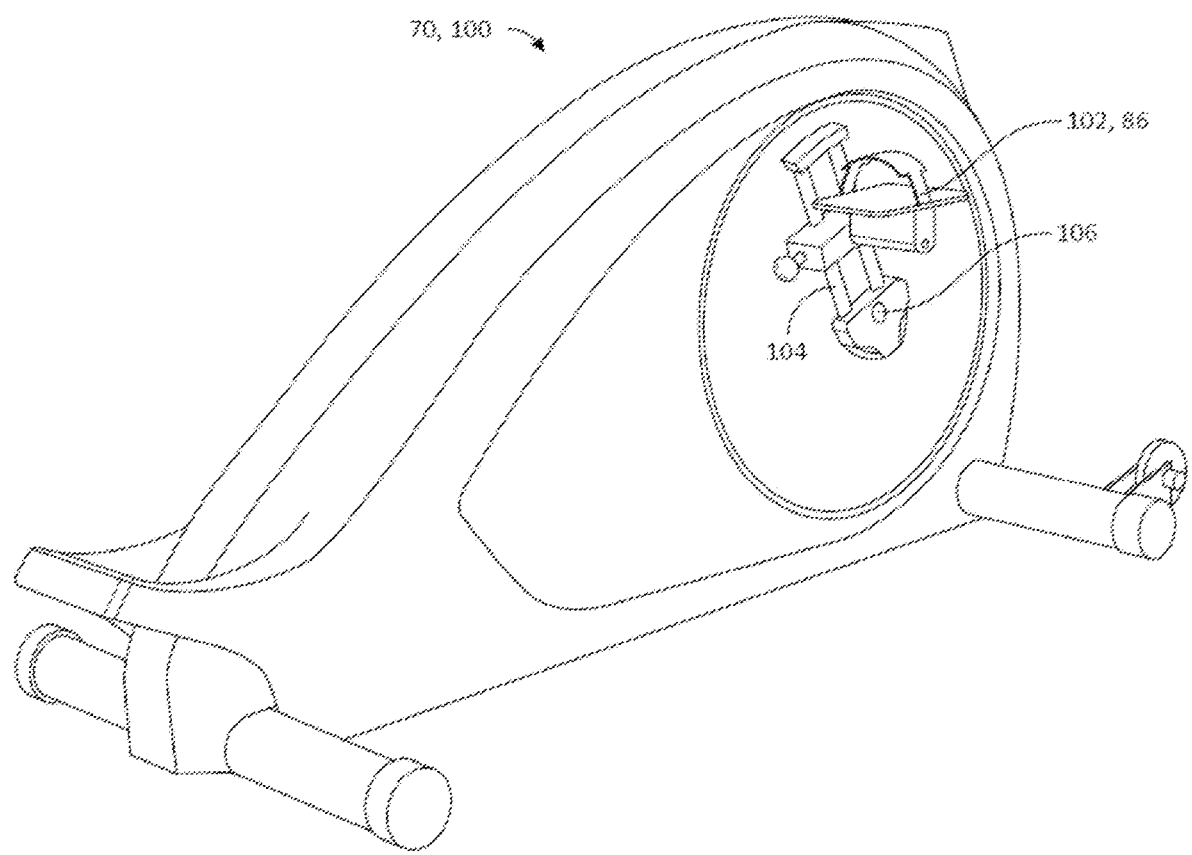
FIG. 2 generally illustrates a perspective view of an embodiment of a treatment device according to principles of the present disclosure.
Figure 3:
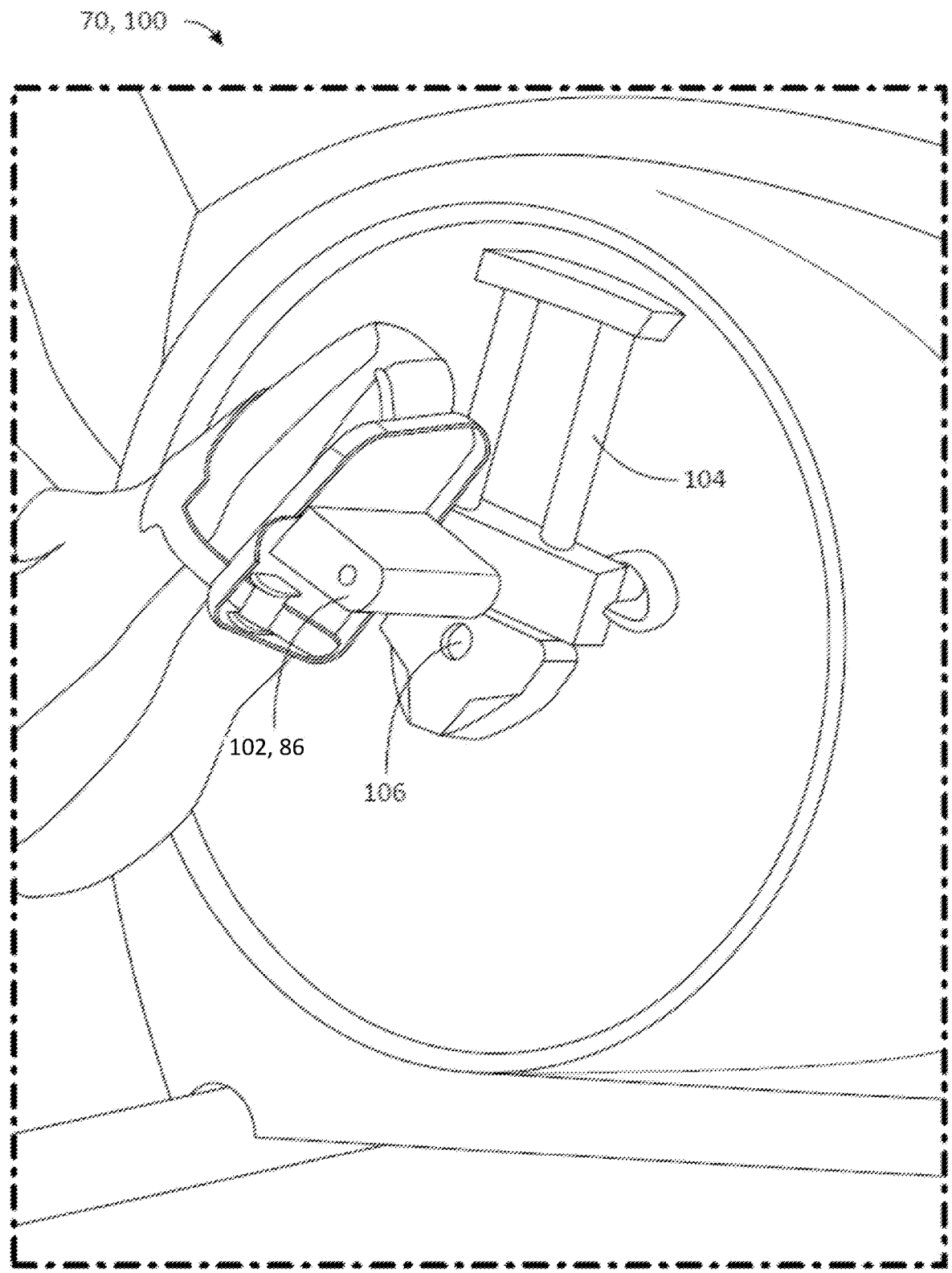
FIG. 3 generally illustrates a perspective view of an embodiment of pedal of the treatment device of FIG. 2 according to principles of the present disclosure.

FIGS. 2-3 show an embodiment of a treatment apparatus 70. More specifically, FIG. 2 shows a treatment apparatus 70 in the form of a stationary cycling machine 100, which may be called a stationary bike, for short. The stationary cycling machine 100 includes a set of pedals 102 each attached to a pedal arm 104 for rotation about an axle 106. In some embodiments, and as shown in FIG. 2, the pedals 102 are movable on the pedal arms 104 in order to adjust a range of motion used by the patient in pedaling. For example, the pedals being located inwardly toward the axle 106 corresponds to a smaller range of motion than when the pedals are located outwardly away from the axle 106. A pressure sensor 86 is attached to or embedded within one of the pedals 102 for measuring an amount of force applied by the patient on the pedal 102. The pressure sensor 86 may communicate wirelessly to the treatment apparatus 70 and/or to the patient interface 50.

Figure 4:
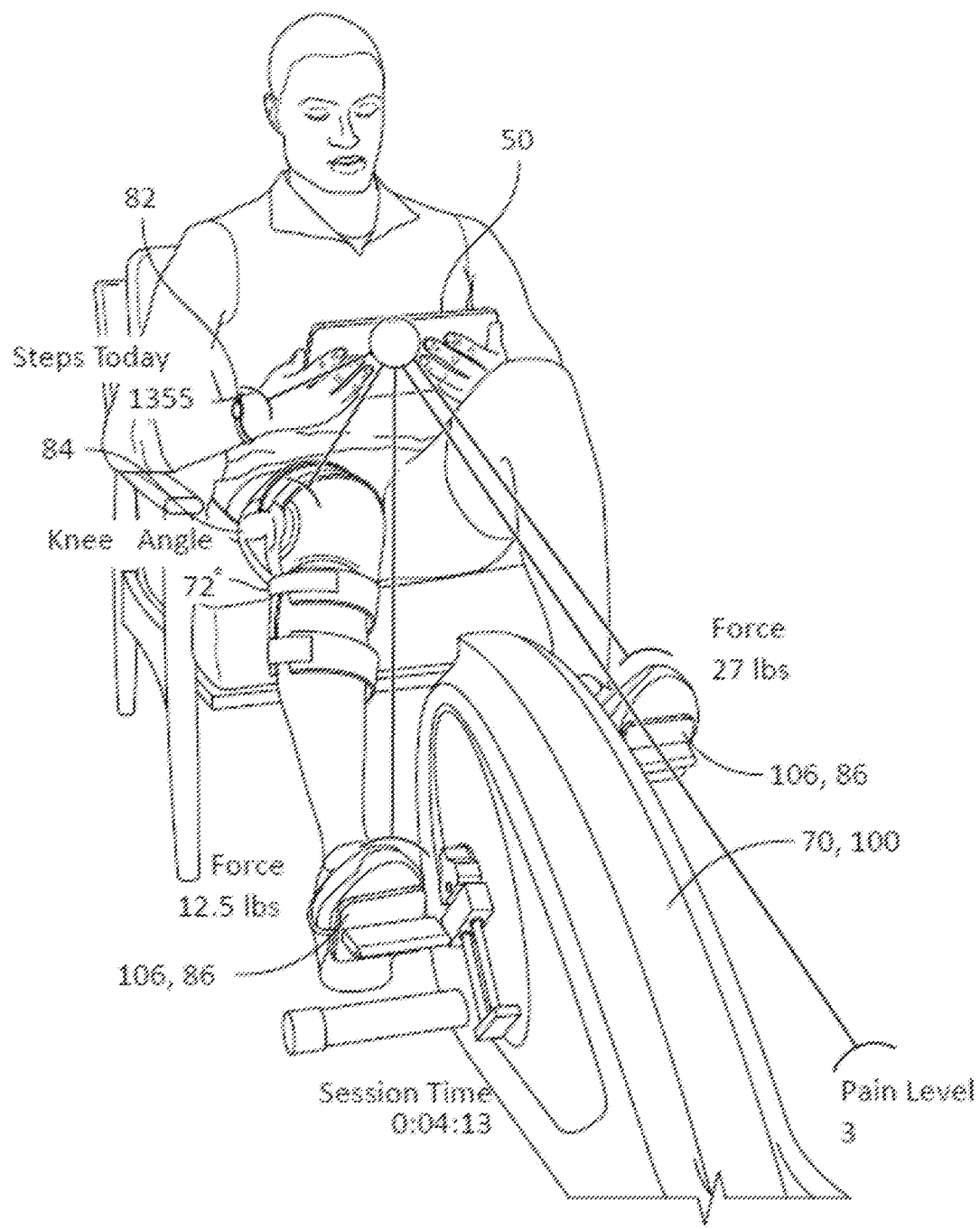
FIG. 4 generally illustrates a perspective view of a person using the treatment device of FIG. 2 according to principles of the present disclosure.

FIG. 4 shows a person (a patient) using the treatment apparatus of FIG. 2, and showing sensors and various data parameters connected to a patient interface 50. The example patient interface 50 may be a tablet computer or smartphone, or a phablet, such as an iPad, an iPhone, an Android device, a Surface tablet, or any other electronic device held manually by the patient. In some other embodiments, the patient interface 50 may be embedded within or attached to the treatment apparatus 70, obviating the need for the patient to hold the device manually, other than for the possible purpose of interacting with it. FIG. 4 shows the patient wearing the ambulation sensor 82 on his wrist, with a note showing "STEPS TODAY 1355", indicating that the ambulation sensor 82 has recorded and transmitted that step count to the patient interface 50. FIG. 4 also shows the patient wearing the goniometer 84 on his right knee, with a note showing "KNEE ANGLE 72° ", indicating that the goniometer 84 is measuring and transmitting that knee angle to the patient interface 50. FIG. 4 also shows a right side of one of the pedals 102 with a pressure sensor 86 showing "FORCE 12.5 lbs.", indicating that the right pedal pressure sensor 86 is measuring and transmitting that force measurement to the patient interface 50. FIG. 4 also shows a left side of one of the pedals 102 with a pressure sensor 86 showing "FORCE 27 lbs.", indicating that the left pedal pressure sensor 86 is measuring and transmitting that force measurement to the patient interface 50. FIG. 4 also shows other patient data, such as an indicator of "SESSION TIME 0:04:13", indicating that the patient has been using the treatment apparatus 70 for 4 minutes and 13 seconds. This session time may be determined by the patient interface 50 based on information received from the treatment apparatus 70. FIG. 4 also shows an indicator showing "PAIN LEVEL 3". Such a pain level may be obtained from the patent in response to a solicitation or inquiry, such as a question, presented upon the patient interface 50.

Figure 5:
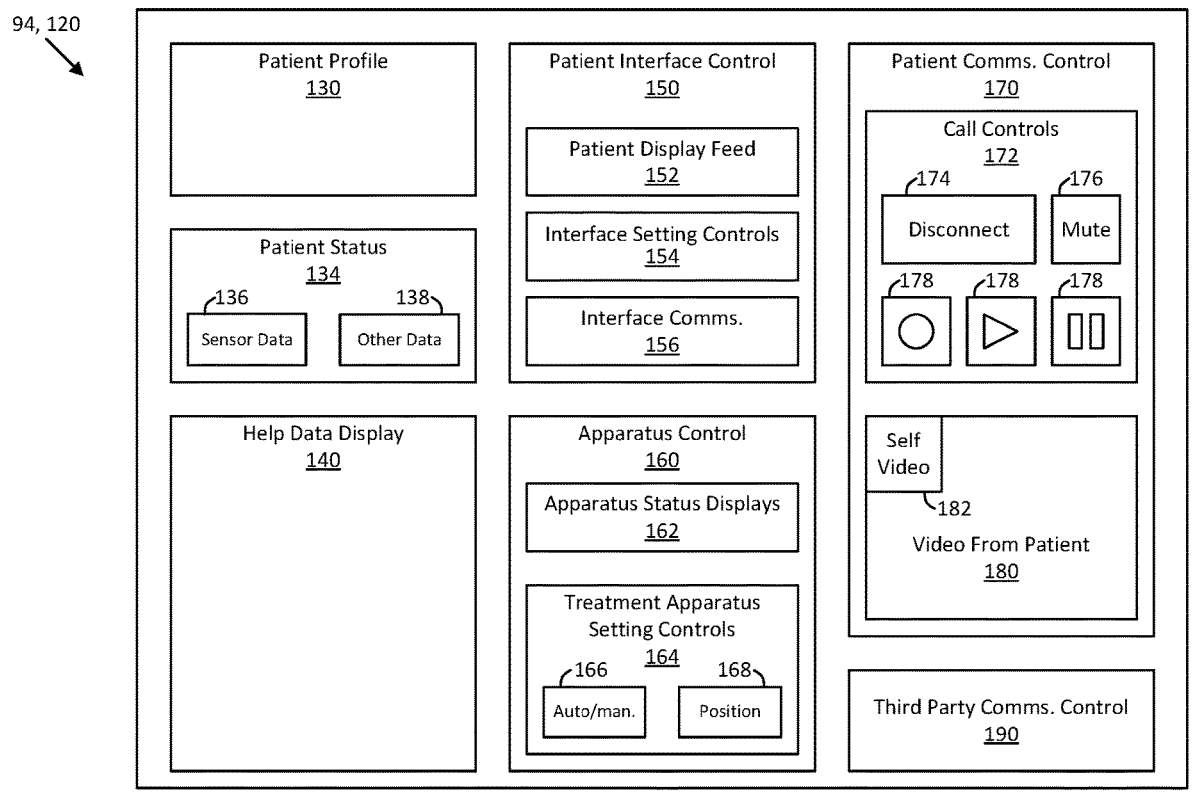
FIG. 5 generally illustrates an example embodiment of an overview display of an assistant interface according to principles of the present disclosure.

FIG. 5 is an example embodiment of an overview display 120 of the assistant interface 94. Specifically, the overview display 120 presents several different controls and interfaces for the assistant to remotely assist a patient with using the patient interface 50 and/or the treatment apparatus 70. This remote assistance functionality may comprise a type of functionality present in telemedicine systems.

Specifically, the overview display 120 includes a patient profile display 130 presenting biographical information regarding a patient using the treatment apparatus 70. The patient profile display 130 may take the form of a portion or region of the overview display 120, as shown in FIG. 5, although the patient profile display 130 may take other forms, such as a separate screen or a popup window. In some embodiments, the patient profile display 130 may include a limited subset of the patient's biographical information, health-related information, or both. More specifically, the data presented upon the patient profile display 130 may depend upon the assistant's need for that information. For example, a healthcare professional assisting the patient with a medical issue may be provided with medical history information regarding the patient, whereas a technician troubleshooting an issue with the treatment apparatus 70 may be provided with a much more limited set of information regarding the patient. The technician, for example, may be given only the patient's name. The patient profile display 130 may include pseudonymized data and/or anonymized data or use any privacy enhancing technology to prevent confidential patient data from being communicated in a way that could violate patient confidentiality requirements. Such privacy enhancing technologies may enable compliance with laws, regulations, or other rules of governance such as, but not limited to, the Health Insurance Portability and Accountability Act (HIPAA), or the General Data Protection Regulation (GDPR), wherein the patient may be deemed a "data subject."

In some embodiments, the patient profile display 130 may present information regarding the treatment plan for the patient to follow in using the treatment apparatus 70. Such treatment plan information may be limited to an assistant who is a healthcare professional, such as a doctor or physical therapist. For example, a healthcare professional assisting the patient with an issue regarding the treatment regimen may be provided with treatment plan information, whereas a technician troubleshooting an issue with the treatment apparatus 70 may not be provided with any information regarding the patient's treatment plan.

In some embodiments, one or more recommended treatment plans and/or excluded treatment plans may be presented in the patient profile display 130 to the assistant. The one or more recommended treatment plans and/or excluded treatment plans may be generated by the artificial intelligence engine 11 of the server 30 and received from the server 30 in real-time during, inter alia, a telemedicine session. An example of presenting the one or more recommended treatment plans and/or ruled-out treatment plans is described below with reference to FIG. 7.

The example overview display 120 shown in FIG. 5 also includes a patient status display 134 presenting status information regarding a patient using the treatment apparatus. The patient status display 134 may take the form of a portion or region of the overview display 120, as shown in FIG. 5, although the patient status display 134 may take other forms, such as a separate screen or a popup window. The patient status display 134 includes sensor data 136 from one or more of the external sensors 82, 84, 86, and/or from one or more internal sensors 76 of the treatment apparatus 70. In some embodiments, the patient status display 134 may present other data 138 regarding the patient, such as last reported pain level, or progress within a treatment plan.

User access controls may be used to limit access, including which data is available to be viewed and/or modified, on any or all of the user interfaces 20, 50, 90, 92, and 94 of the system 10. In some embodiments, user access controls may be employed to control which information is available to any given person, wherein the given person is using the system 10. For example, data presented on the assistant interface 94 may be controlled by user access controls, with permissions set depending on the assistant/user's need for and/or qualifications to view that information.

The example overview display 120 shown in FIG. 5 also includes a help data display 140 presenting information for the assistant to use in assisting the patient. The help data display 140 may take the form of a portion or region of the overview display 120, as shown in FIG. 5. The help data display 140 may take other forms, such as a separate screen or a popup window. The help data display 140 may include, for example, presenting answers to frequently asked questions regarding use of the patient interface 50 and/or the treatment apparatus 70. The help data display 140 may also include research data or best practices. In some embodiments, the help data display 140 may present scripts for answers or explanations in response to patient questions. In some embodiments, the help data display 140 may present flow charts or walk-throughs for the assistant to use in determining a root cause and/or solution to a patient's problem. In some embodiments, the assistant interface 94 may present two or more help data displays 140, which may be the same or different, for simultaneous presentation of help data for use by the assistant. For example, a first help data display may be used to present a troubleshooting flowchart to determine the source of a patient's problem, and a second help data display may present script information for the assistant to read to the patient, such information to preferably include directions for the patient to perform some action, which may help to narrow down or solve the problem. In some embodiments, based upon inputs to the troubleshooting flowchart in the first help data display, the second help data display may automatically populate with script information.

The example overview display 120 shown in FIG. 5 also includes a patient interface control 150 presenting information regarding the patient interface 50, and/or for modifying one or more settings of the patient interface 50. The patient interface control 150 may take the form of a portion or region of the overview display 120, as shown in FIG. 5. The patient interface control 150 may take other forms, such as a separate screen or a popup window. The patient interface control 150 may present information communicated to the assistant interface 94 via one or more of the interface monitor signals 98b. As shown in FIG. 5, the patient interface control 150 includes a display feed 152 of the display presented by the patient interface 50. In some embodiments, the display feed 152 may include a live copy of the display screen currently being presented to the patient by the patient interface 50. In other words, the display feed 152 may present an image of what is presented on a display screen of the patient interface 50. In some embodiments, the display feed 152 may include abbreviated information regarding the display screen currently being presented by the patient interface 50, such as a screen name or a screen number. The patient interface control 150 may include a patient interface setting control 154 for the assistant to adjust or to control one or more settings or aspects of the patient interface 50. In some embodiments, the patient interface setting control 154 may cause the assistant interface 94 to generate and/or to transmit an interface control signal 98 for controlling a function or a setting of the patient interface 50.

In some embodiments, the patient interface setting control 154 may include a collaborative browsing or co-browsing capability for the assistant to remotely view and/or control the patient interface 50. For example, the patient interface setting control 154 may enable the assistant to remotely enter text to one or more text entry fields on the patient interface 50 and/or to remotely control a cursor on the patient interface 50 using a mouse or touchscreen of the assistant interface 94.

In some embodiments, using the patient interface 50, the patient interface setting control 154 may allow the assistant to change a setting that cannot be changed by the patient. For example, the patient interface 50 may be precluded from enabling access to a language setting in order to prevent a patient from inadvertently switching, on the patient interface 50, the language used for the displays, whereas the patient interface setting control 154 may enable the assistant to change the language setting of the patient interface 50. In another example, the patient interface 50 may not be able to change a font size setting to a smaller size in order to prevent a patient from inadvertently switching the font size used for the displays on the patient interface 50 such that the display would become illegible or unintelligible to the patient, whereas the patient interface setting control 154 may provide for the assistant to change the font size setting of the patient interface 50.

The example overview display 120 shown in FIG. 5 also includes an interface communications display 156 showing the status of communications between the patient interface 50 and one or more other devices 70, 82, 84, such as the treatment apparatus 70, the ambulation sensor 82, and/or the goniometer 84. The interface communications display 156 may take the form of a portion or region of the overview display 120, as shown in FIG. 5. The interface communications display 156 may take other forms, such as a separate screen or a popup window. The interface communications display 156 may include controls for the assistant to remotely modify communications with one or more of the other devices 70, 82, 84. For example, the assistant may remotely command the patient interface 50 to reset communications with one of the other devices 70, 82, 84, or to establish communications with a new or replacement one of the other devices 70, 82, 84. This functionality may be used, for example, where the patient has a problem with one of the other devices 70, 82, 84, or where the patient receives a new or a replacement one of the other devices 70, 82, 84.

The example overview display 120 shown in FIG. 5 also includes an apparatus control 160 for the assistant to view and/or to control information regarding the treatment apparatus 70. The apparatus control 160 may take the form of a portion or region of the overview display 120, as shown in FIG. 5. The apparatus control 160 may take other forms, such as being enabled through or presented on a separate screen or a popup window. The apparatus control 160 may include an apparatus status display 162 with information regarding the current status of the apparatus. The apparatus status display 162 may present information communicated to the assistant interface 94 via one or more of the apparatus monitor signals 99b. The apparatus status display 162 may indicate whether the treatment apparatus 70 is currently communicating with the patient interface 50. The apparatus status display 162 may present other current and/or historical information regarding the status of the treatment apparatus 70.

The apparatus control 160 may include an apparatus setting control 164 for the assistant to adjust or control one or more aspects of the treatment apparatus 70. The apparatus setting control 164 may cause the assistant interface 94 to generate and/or to transmit an apparatus control signal 99 for changing an operating parameter of the treatment apparatus 70 (e.g., a pedal radius setting, a resistance setting, a target RPM, etc.). The apparatus setting control 164 may include a mode button 166 and a position control 168, which may be used in conjunction for the assistant to place an actuator 78 of the treatment apparatus 70 in a manual mode, after which a setting, such as a position or a speed of the actuator 78, can be changed using the position control 168. The mode button 166 may provide for a setting, such as a position, to be toggled between automatic and manual modes. In some embodiments, one or more settings may be adjustable at any time, but without a necessity of having an associated auto/manual mode. In some embodiments, the assistant may change an operating parameter of the treatment apparatus 70, such as a pedal radius setting, while the patient is actively using the treatment apparatus 70. Such "on the fly" adjustment may or may not be available to the patient using the patient interface 50. In some embodiments, the apparatus setting control 164 may allow the assistant to change a setting that cannot be changed by the patient using the patient interface 50. For example, the patient interface 50 may be precluded from changing a preconfigured setting, such as a height or a tilt setting of the treatment apparatus 70, whereas the apparatus setting control 164 may provide for the assistant to change the height or tilt setting of the treatment apparatus 70.

The example overview display 120 shown in FIG. 5 also includes a patient communications control 170 for controlling an audio or an audiovisual communications session with the patient interface 50. The communications session with the patient interface 50 may comprise a live feed from the assistant interface 94 for presentation on or by the output device of the patient interface 50. The live feed may take the form of an audio feed and/or a video feed. In some embodiments, the patient interface 50 may be configured to provide two-way audio or audiovisual communications with a person using the assistant interface 94. Specifically, the communications session with the patient interface 50 may include bidirectional (two-way) video or audiovisual feeds, with each of the patient interface 50 and the assistant interface 94 presenting video of the other one. In some embodiments, the patient interface 50 may present video from the assistant interface 94, while the assistant interface 94 presents only audio or the assistant interface 94 presents no live audio or visual signal from the patient interface 50. In some embodiments, the assistant interface 94 may present video from the patient interface 50, while the patient interface 50 presents only audio or the patient interface 50 presents no live audio or visual signal from the assistant interface 94.

In some embodiments, the audio or an audiovisual communications session with the patient interface 50 may take place, at least in part, while the patient is performing the rehabilitation regimen upon the body part. The patient communications control 170 may take the form of a portion or region of the overview display 120, as shown in FIG. 5. The patient communications control 170 may take other forms, such as being enabled by or on a separate screen or a popup window. The audio and/or audiovisual communications may be processed and/or directed by the assistant interface 94 and/or by another device or devices, such as a telephone system, or a videoconferencing system (e.g., Zoom, WebEx, etc.) used by the assistant while the assistant uses the assistant interface 94. Alternatively or additionally, the audio and/or audiovisual communications may include communications with a third party. For example, the system 10 may enable the assistant to initiate a 3-way conversation with the patient and a subject matter expert, such as a healthcare professional or a specialist, regarding use of a particular piece of hardware or software. The example patient communications control 170 shown in FIG. 5 includes call controls 172 for the assistant to use in managing various aspects of the audio or audiovisual communications with the patient. The call controls 172 include a disconnect button 174 for the assistant to end the audio or audiovisual communications session. The call controls 172 also include a mute button 176 to temporarily mute or attenuate an audio or audiovisual signal from the assistant interface 94. In some embodiments, the call controls 172 may include other features, such as a hold button (not shown). The call controls 172 may also include one or more record/playback controls 178, such as record, play, and pause buttons to control, with the patient interface 50, recording and/or playback of audio and/or video from the teleconference session. The call controls 172 may also include a video feed display 180 for presenting still and/or video images from the patient interface 50, and a self-video display 182 for showing the current image of the assistant using the assistant interface. The self-video display 182 may be presented as a picture-in-picture (PiP) format, such PiP format being within a section of the video feed display 180, as shown in FIG. 5. Alternatively or additionally, the self-video display 182 may be presented separately and/or independently from the video feed display 180.

The example overview display 120 shown in FIG. 5 also includes a third party communications control 190 for use in conducting audio and/or audiovisual communications with a third party. The third party communications control 190 may take the form of a portion or region of the overview display 120, as shown in FIG. 5. The third party communications control 190 may take other forms, such as enabling or presenting on a display on a separate screen or a popup window. The third party communications control 190 may include one or more controls, such as a contact list and/or buttons or controls to contact a third party regarding use of a particular piece of hardware or software, e.g., a subject matter expert, such as a healthcare professional or a specialist. The third party communications control 190 may include a conference-calling capability for the third party to simultaneously communicate with both the assistant via the assistant interface 94, and the patient via the patient interface 50. For example, the system 10 may provide for the assistant to initiate a 3-way conversation with the patient and the third party.

Figure 6:
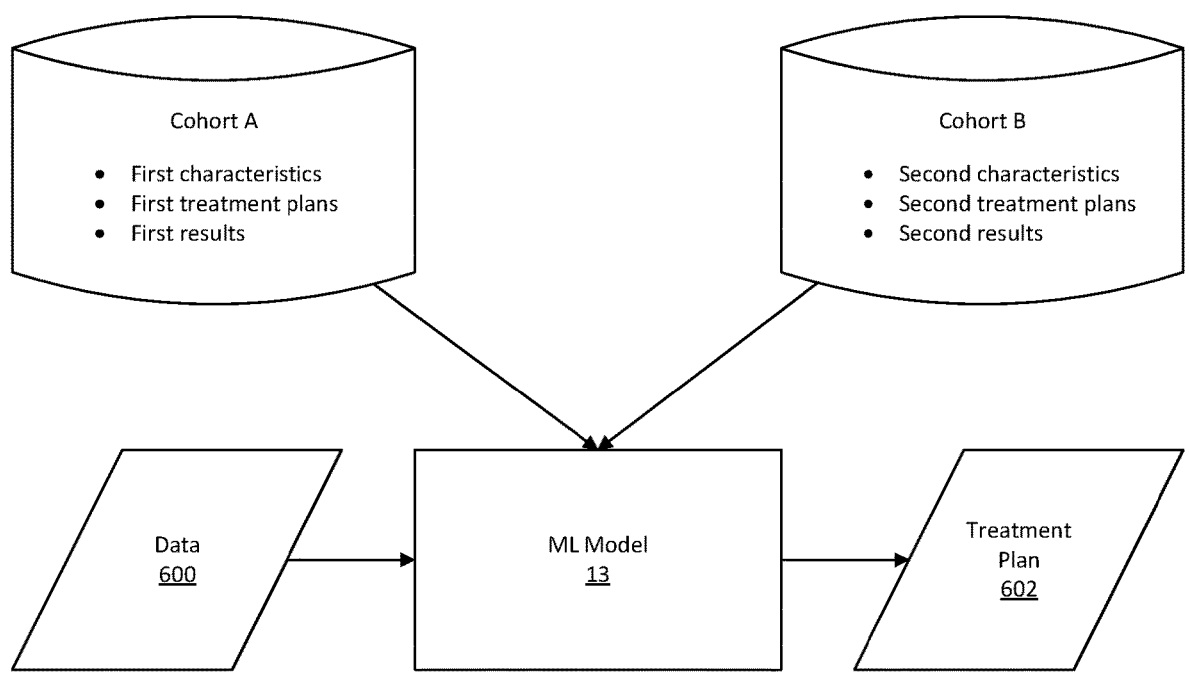
FIG. 6 generally illustrates an example block diagram of training a machine learning model to output, based on data pertaining to the patient, a treatment plan for the patient according to principles of the present disclosure.

FIG. 6 shows an example block diagram of training a machine learning model 13 to output, based on data 600 pertaining to the patient, a treatment plan 602 for the patient according to the present disclosure. Data pertaining to other patients may be received by the server 30. The other patients may have used various treatment apparatuses to perform treatment plans. The data may include characteristics of the other patients, the details of the treatment plans performed by the other patients, and/or the results of performing the treatment plans (e.g., a percentage of recovery of a portion of the patients' bodies, an amount of recovery of a portion of the patients' bodies, an amount of increase or decrease in muscle strength of a portion of patients' bodies, an amount of increase or decrease in range of motion of a portion of patients' bodies, etc.).

As depicted in FIG. 6, the data has been assigned to different cohorts. Cohort A includes data for patients having similar first characteristics, first treatment plans, and first results. Cohort B includes data for patients having similar second characteristics, second treatment plans, and second results. For example, cohort A may include first characteristics of patients in their twenties without any medical conditions, and wherein such patients underwent surgery for a broken limb; their treatment plans may include a certain treatment protocol (e.g., use the treatment apparatus 70 for 30 minutes 5 times a week for 3 weeks, wherein values for the properties, configurations, and/or settings of the treatment apparatus 70 are set to X (where X is a numerical value) for the first two weeks and to Y (where Y is a numerical value) for the last week).

As further depicted in FIG. 6, Cohort A and cohort B may be included in a training dataset used to train the machine learning model 13. The machine learning model 13 may be trained to match a pattern between one or more characteristics for each cohort and output the treatment plan that provides the result, i.e., the best match. Accordingly, when the data 600 for a new patient is input into the trained machine learning model 13, the trained machine learning model 13 may match the one or more characteristics included in the data 600 with one or more characteristics in either cohort A or cohort B and output the appropriate treatment plan 602. In some embodiments, the machine learning model 13 may be trained to output one or more excluded treatment plans that should not be performed by the new patient.

Figure 7:
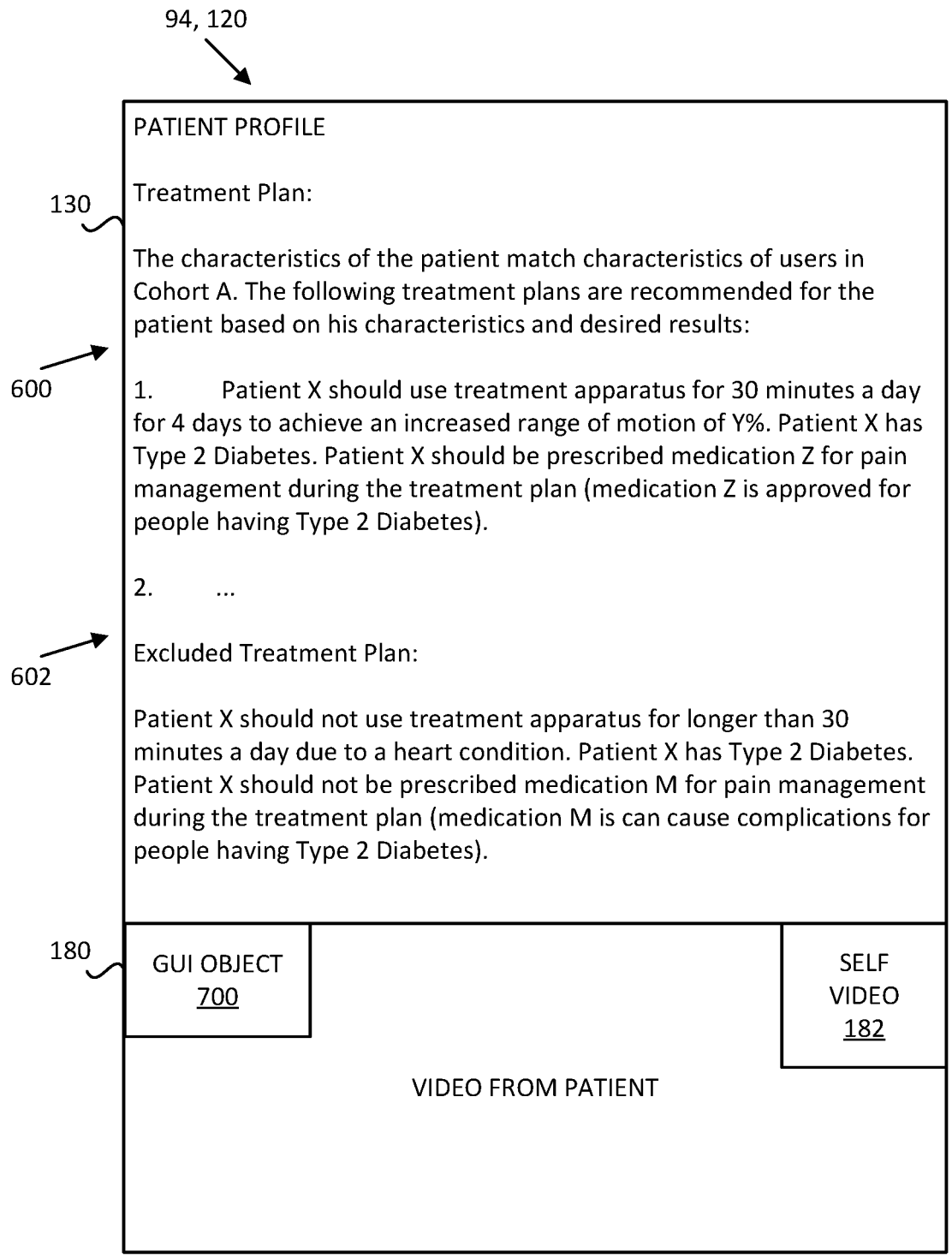
FIG. 7 generally illustrates an example overview display of the assistant interface presenting recommended treatment plans and excluded treatment plans in real-time during a telemedicine session according to principles of the present disclosure.

FIG. 7 shows an embodiment of an overview display 120 of the assistant interface 94 presenting in real-time during a telemedicine session recommended treatment plans and excluded treatment plans according to the present disclosure. As depicted in FIG. 7, the overview display 120 just includes sections for the patient profile 130 and the video feed display 180, including the self-video display 182. Any suitable configuration of controls and interfaces of the overview display 120 described with reference to FIG. 5 may be presented in addition to or instead of the patient profile 130, the video feed display 180, and the self-video display 182.

As further depicted in FIG. 7, the assistant (e.g., healthcare professional) using the assistant interface 94 (e.g., computing device) during the telemedicine session may be presented in the self-video 182 in a portion of the overview display 120 (e.g., user interface presented on a display screen 24 of the assistant interface 94) that also presents a video from the patient in the video feed display 180. Further, the video feed display 180 may also include a graphical user interface (GUI) object 700 (e.g., a button) that enables the healthcare professional to share on the patient interface 50, in real-time or near real-time during the telemedicine session, the recommended treatment plans and/or the excluded treatment plans with the patient. The healthcare professional may select the GUI object 700 to share the recommended treatment plans and/or the excluded treatment plans. As depicted, another portion of the overview display 120 includes the patient profile display 130.

The patient profile display 130 illustrated in FIG. 7 presents two example recommended treatment plans 600 and one example excluded treatment plan 602. As described herein, the treatment plans may be recommended in view of characteristics of the patient being treated. To generate the recommended treatment plans 600 the patient should follow to achieve a desired result, a pattern between the characteristics of the patient being treated and a cohort of other patients who have used the treatment apparatus 70 to perform a treatment plan may be matched by one or more machine learning models 13 of the artificial intelligence engine 11. Each of the recommended treatment plans may be generated based on different desired results, i.e., different desired outcomes or best matches.

For example, as depicted in FIG. 7, the patient profile display 130 presents "The characteristics of the patient match characteristics of patients in Cohort A. The following treatment plans are recommended for the patient based on his characteristics and desired results." Then, the patient profile display 130 presents recommended treatment plans from cohort A, and each treatment plan provides different results.

As depicted in FIG. 7, treatment plan "1" indicates "Patient X should use treatment apparatus for 30 minutes a day for 4 days to achieve an increased range of motion of Y %; Patient X has Type 2 Diabetes; and Patient X should be prescribed medication Z for pain management during the treatment plan (medication Z is approved for patients having Type 2 Diabetes)." Accordingly, the treatment plan generated achieves increasing the range of motion of Y %. As may be appreciated, the treatment plan also includes a recommended medication (e.g., medication Z) to prescribe to the patient to manage pain in view of a known medical disease (e.g., Type 2 Diabetes) of the patient. That is, the recommended patient medication not only does not conflict with the medical condition of the patient but thereby improves the probability of a superior patient outcome. This specific example and all such examples elsewhere herein are not intended to limit in any way the generated treatment plan from recommending multiple medications, or from handling the acknowledgement, view, diagnosis and/or treatment of comorbid conditions or diseases.

As illustrated in FIG. 7, recommended treatment plan "2" may specify, based on a different desired result of the treatment plan, a different treatment plan including a different treatment protocol for a treatment apparatus, a different medication regimen, etc.

As depicted in FIG. 7, the patient profile display 130 may also present the excluded treatment plans 602. These types of treatment plans are shown to the assistant using the assistant interface 94 to alert the assistant not to recommend certain portions of a treatment plan to the patient. For example, the excluded treatment plan could specify the following: "Patient X should not use treatment apparatus for longer than 30 minutes a day due to a heart condition; Patient X has Type 2 Diabetes; and Patient X should not be prescribed medication M for pain management during the treatment plan (in this scenario, medication M can cause complications for patients having Type 2 Diabetes). Specifically, the excluded treatment plan points out a limitation of a treatment protocol where, due to a heart condition, Patient X should not exercise for more than 30 minutes a day. The ruled-out treatment plan also points out that Patient X should not be prescribed medication M because it conflicts with the medical condition Type 2 Diabetes.

As further depicted in FIG. 7, the assistant may select the treatment plan for the patient on the overview display 120. For example, the assistant may use an input peripheral (e.g., mouse, touchscreen, microphone, keyboard, etc.) to select from the treatment plans 600 for the patient. In some embodiments, during the telemedicine session, the assistant may discuss the pros and cons of the recommended treatment plans 600 with the patient.

In any event, the assistant may select, as depicted in FIG. 7, the treatment plan for the patient to follow to achieve the desired result. The selected treatment plan may be transmitted to the patient interface 50 for presentation. The patient may view the selected treatment plan on the patient interface 50. In some embodiments, the assistant and the patient may discuss during the telemedicine session the details (e.g., treatment protocol using treatment apparatus 70, diet regimen, medication regimen, etc.) in real-time or in near real-time. In some embodiments, the server 30 may control, based on the selected treatment plan and during the telemedicine session, the treatment apparatus 70 as the user uses the treatment apparatus 70.

Figure 8:
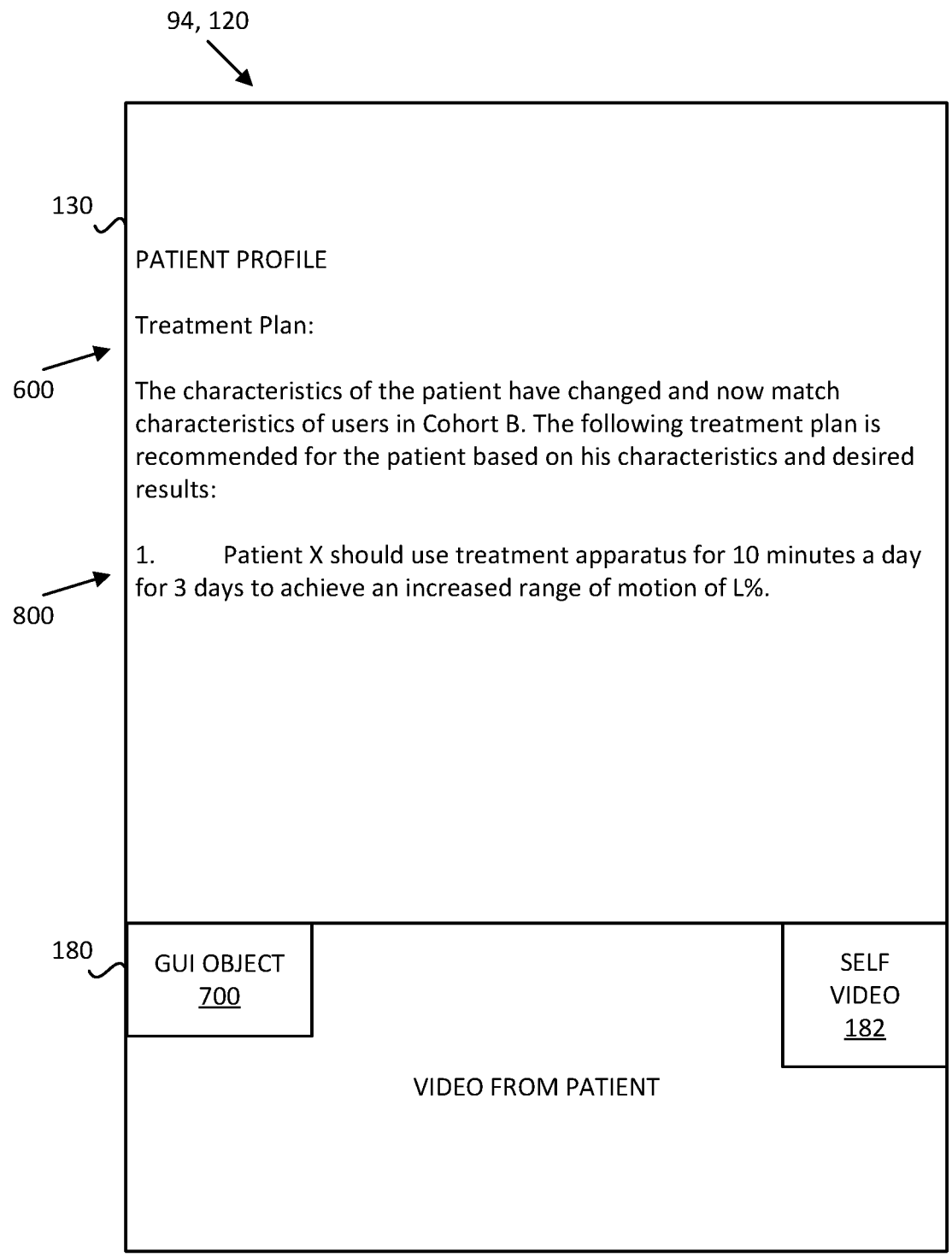
FIG. 8 generally illustrates an example overview display of the assistant interface presenting, in real-time during a telemedicine session, recommended treatment plans that have changed as a result of patient data changing according to principles of the present disclosure.

FIG. 8 shows an embodiment of the overview display 120 of the assistant interface 94 presenting, in real-time during a telemedicine session, recommended treatment plans that have changed due to patient data changing according to the present disclosure. As may be appreciated, the treatment apparatus 70 and/or any computing device (e.g., patient interface 50) may transmit data while the patient uses the treatment apparatus 70 to perform a treatment plan. The data may include updated characteristics of the patient. For example, the updated characteristics may include new performance information and/or measurement information related to the patient, the apparatus, the environment, etc. The performance information may include a speed of a portion of the treatment apparatus 70, a range of motion achieved by the patient, a force exerted on a portion of the treatment apparatus 70, a heartrate of the patient, a blood pressure of the patient, a respiratory rate of the patient, and so forth.

In one embodiment, the data received at the server 30 may be input into the trained machine learning model 13, which may determine that the characteristics indicate the patient is on track to achieve one or more goals associated with or part of the current treatment plan. Determining the patient is on track for the current treatment plan may cause the trained machine learning model 13 to adjust a parameter of the treatment apparatus 70. The adjustment may be based on a next step of the treatment plan to further improve the performance of the patient during that next step so as to more quickly achieve the one or more goals associated with or part of the current treatment plan or to surpass said one or more goals based on the adjustment.

In one embodiment, the data received at the server 30 may be input into the trained machine learning model 13, which may determine that the characteristics indicate the patient is not on track (e.g., behind schedule, not able to maintain a speed, not able to achieve a certain range of motion, is in too much pain, etc.) for the current treatment plan or is ahead of schedule (e.g., exceeding a certain speed, exercising longer than specified with no pain, exerting more than a specified force, etc.) for the current treatment plan. The trained machine learning model 13 may determine, due to the patient's not being on track or being ahead of schedule, that the characteristics of the patient no longer match the characteristics of the patients in the cohort to which the patient is assigned. Accordingly, the trained machine learning model 13 may reassign the patient to another cohort that includes as qualifying characteristics the patient's then-current characteristics. As such, the trained machine learning model 13 may select a new treatment plan from the new cohort and control, based on the new treatment plan, the treatment apparatus 70. In some embodiments, the trained machine learning model 13 may directly control the treatment apparatus 70 based on the new treatment plan. In other embodiments, the trained machine learning model 13 may control the treatment apparatus 70 based on the new treatment plan by updating one or more programs being executed on the treatment apparatus 70 itself.

In some embodiments, prior to controlling the treatment apparatus 70, the server 30 may provide the new treatment plan 800 to the assistant interface 94 for presentation in the patient profile 130. As depicted in FIG. 8, the patient profile 130 indicates "The characteristics of the patient have changed and now match characteristics of patients in Cohort B. The following treatment plan is recommended for the patient based on his characteristics and desired results." Then, the patient profile 130 presents the new treatment plan 800 ("Patient X should use treatment apparatus for 10 minutes a day for 3 days to achieve an increased range of motion of L %"). The assistant (healthcare professional) may select the new treatment plan 800, and the server 30 may receive the selection. The server 30 may control the treatment apparatus 70 based on the new treatment plan 800. In some embodiments, the new treatment plan 800 may be transmitted to the patient interface 50 such that the patient may view the details of the new treatment plan 800.

Figure 9:
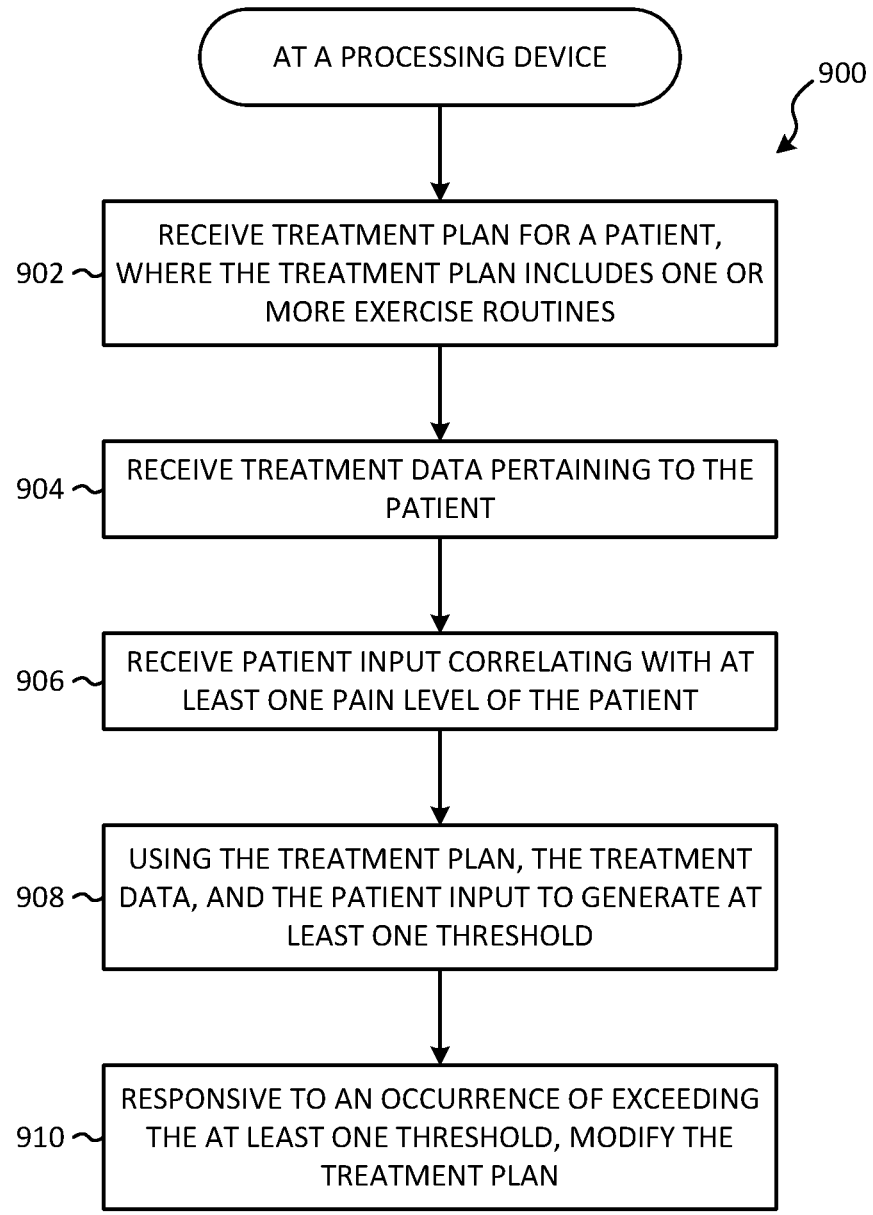
FIG. 9 is a flow diagram generally illustrating a method for modifying, by an artificial intelligence engine, a treatment plan for optimizing patient outcome and pain levels during one or more treatment sessions according to principles of the present disclosure.

FIG. 9 shows an example embodiment of a method 900 for modifying, by an artificial intelligence engine, a treatment plan for optimizing patient outcome and pain levels during one or more treatment sessions according to the present disclosure. The method 900 is performed by processing logic that may include hardware (circuitry, dedicated logic, etc.), software (such as is run on a general-purpose computer system or a dedicated machine), or a combination of both. The method 900 and/or each of its individual functions, routines, subroutines, or operations may be performed by one or more processors of a computing device (e.g., any component of FIG. 1, such as server 30 executing the artificial intelligence engine 11). In certain implementations, the method 900 may be performed by a single processing thread. Alternatively, the method 900 may be performed by two or more processing threads, each thread implementing one or more individual functions, routines, subroutines, or operations of the methods.

For simplicity of explanation, the method 900 is depicted in FIG. 9 and described as a series of operations. However, operations in accordance with this disclosure can occur in various orders and/or concurrently, and/or with other operations not presented and described herein. For example, the operations depicted in the method 900 in FIG. 9 may occur in combination with any other operation of any other method disclosed herein. Furthermore, not all illustrated operations may be required to implement the method 900 in accordance with the disclosed subject matter. In addition, those skilled in the art will understand and appreciate that the method 900 could alternatively be represented as a series of interrelated states via a state diagram or event diagram.

At block 902, the processing device may receive a treatment plan for a patient. The treatment plan may include one or more exercise routines. In some embodiments, the treatment plane may include one or more exercise routines for the patient to perform on a treatment device or treatment apparatus (e.g. on treatment apparatus 70).

At block 904, the processing device may receive treatment data pertaining to the patient. Treatment data may include, for example, characteristics of the patient, measurement information pertaining to the patient while the patient uses the treatment device, characteristics of the treatment device, the treatment plan, or a combination thereof. Characteristics of the patient may include, for example, age, health history, fitness level, etc. The measurement information may include, for example, one or more vital signs of the user, a respiration rate of the user, a heartrate of the user, a temperature of the user, a blood pressure of the user, other suitable measurement information of the user, or a combination thereof. Various characteristics of the treatment device may include, for example, one or more settings of the treatment device, a current revolutions per minute of a rotating member (e.g., such as a wheel) of the treatment device, a resistance setting of the treatment device, an angular or rotational velocity of the treatment device or components thereof, other suitable characteristics of the treatment device, or a combination thereof.

At block 906, the processing device may receive patient input correlating with at least one pain level of the patient. Patient input may also include, for example, a patient goal, an exhaustion level, etc. The patient may have different pain levels for different parts of the patient's body (e.g., a double knee replacement wherein one knee is recovering faster than the other).

At block 908, the processing device may use the treatment plan, the treatment data, and the patient input to generate at least one threshold. For example, the processing device may generate one or more thresholds described previously herein.

At block 910, responsive to an occurrence (e.g., detecting an occurrence) of exceeding the at least one threshold, the treatment plan may be modified. For example, in some embodiments, at least one updated exercise routine during one of the one or more treatment sessions is generated.

Further, the treatment plan may be modified according to one or more of the examples described previously herein.

In some embodiments, the processing device may control, based on the modified treatment plan, the treatment device while the patient uses the treatment device (e.g., during a telemedicine session). For example, the processing device may cause the treatment device to modify at least one of a volume, a pressure, a resistance, an angle, an angular or rotational velocity, a speed, and a time period. A patient's use of a treatment device may include uses in a clinician's office, in a physical therapy center, in a gym, in a home office, at home, in an exercise or other workout studio, or any of the foregoing when directed by a clinician or person distal to the location of the treatment device, such as when the direction is for the purposes of telemedicine.

Figure 10:
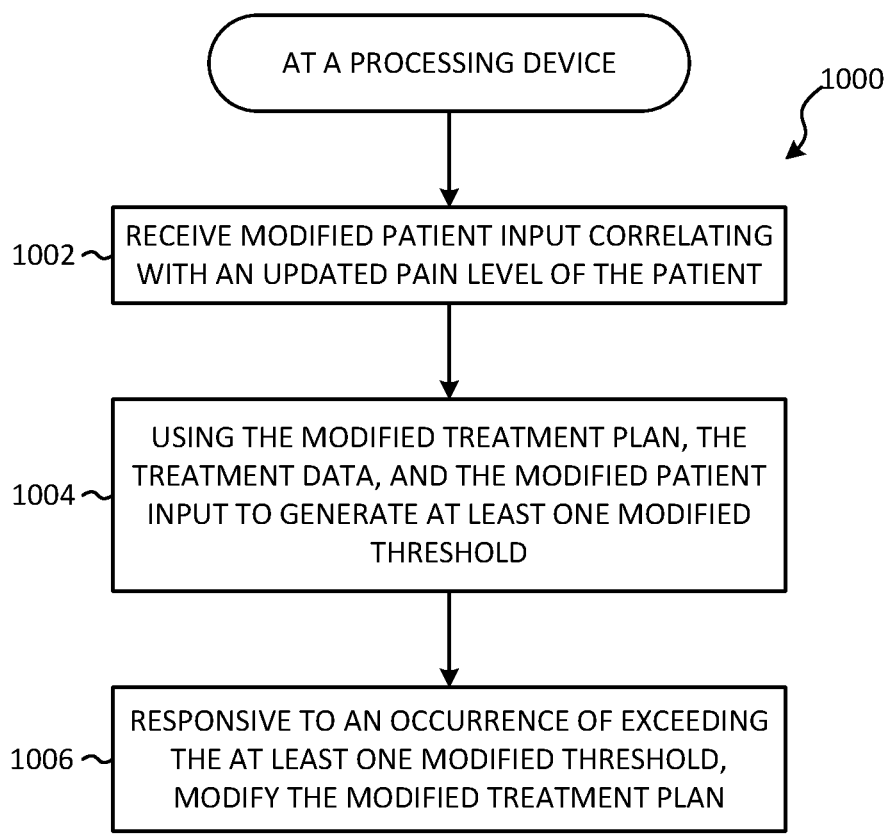
FIG. 10 is a flow diagram generally illustrating a method for further modifying a treatment plan for optimizing patient outcome and pain levels, by an artificial intelligence engine, during one or more treatment sessions using updated pain levels according to principles of the present disclosure.

FIG. 10 shows an example embodiment of a method 1000 for further modifying the treatment plan, by an artificial intelligence engine, using one or more updated pain levels of the patient according to the present disclosure. The method 1000 includes operations performed by processors of a computing device (e.g., any component of FIG. 1, such as server 30 executing the artificial intelligence engine 11). In some embodiments, one or more operations of the method 1000 are implemented in computer instructions stored on a memory device and executed by a processing device. The method 1000 may be performed in the same or a similar manner as described above in regard to method 900. The operations of the method 1000 may be performed in some combination with any of the operations of any of the methods described herein. In some embodiments, the method 1000 may occur after block 910 in the method 900 depicted in FIG. 9. That is, the method 1000 may occur after the treatment plan is modified responsive to an occurrence of exceeding the determined threshold.

Regarding the method 1000, at block 1002, the processing device may receive modified patient input correlating with an updated pain level of the patient. At block 1004, the processing device may use the modified treatment plan, the treatment data, and the modified patient input to generate at least one modified threshold. At block 1006, responsive to an occurrence of exceeding the at least one modified threshold, the modified treatment plan may be modified (e.g., further modified). In some embodiments, the difficulty of the treatment plan may be changed based on the patient's pain level. For example, if the pain level is low or nonexistent, then the difficulty of the workout may be increased for the patient to recover faster. However, if there is too much pain, then the difficulty of the workout may be decreased to decrease the patient's pain level during the exercise session.

Figure 11:
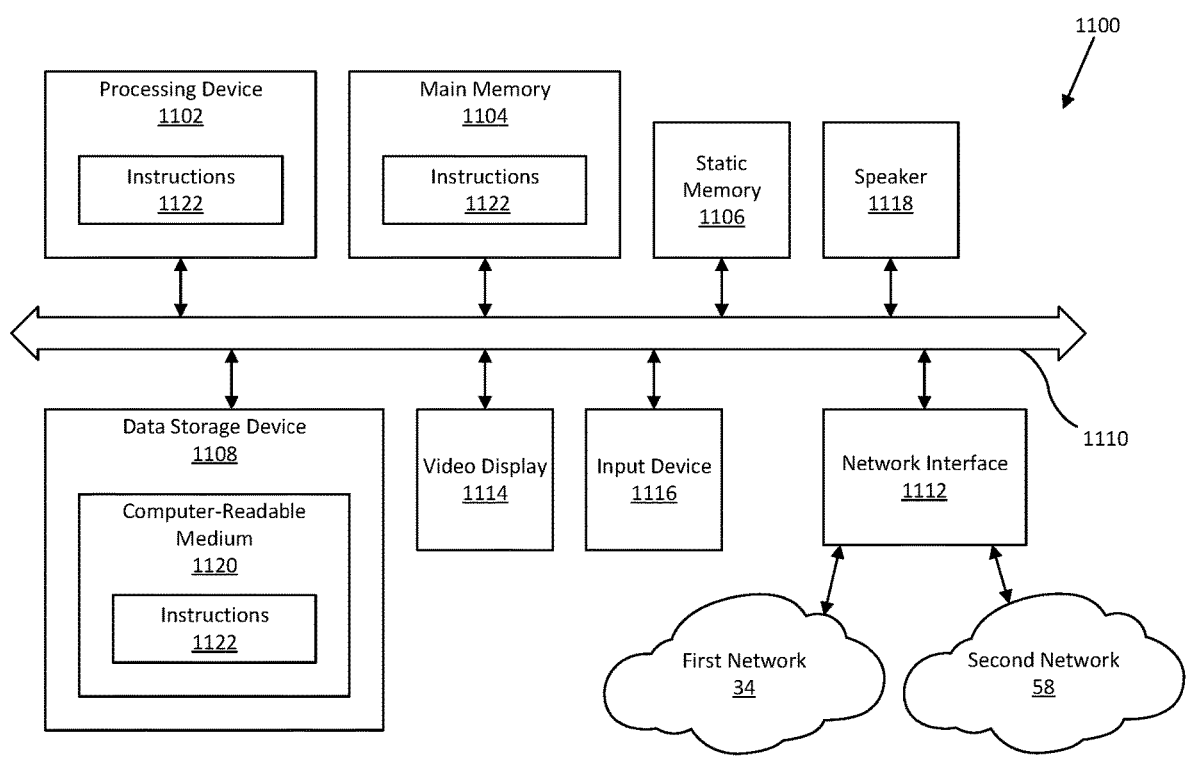
FIG. 11 generally illustrates a computer system according to principles of the present disclosure.

FIG. 11 shows an example computer system 1100 which can perform any one or more of the methods described herein, in accordance with one or more aspects of the present disclosure. In one example, computer system 1100 may include a computing device and correspond to one or more of the assistance interface 94, reporting interface 92, supervisory interface 90, clinician interface 20, server 30 (including the AI engine 11), patient interface 50, ambulatory sensor 82, goniometer 84, treatment apparatus 70, pressure sensor 86, or any suitable component of FIG. 1. The computer system 1100 may be capable of executing instructions implementing the one or more machine learning models 13 of the artificial intelligence engine 11 of FIG. 1. The computer system may be connected (e.g., networked) to other computer systems in a LAN, an intranet, an extranet, or the Internet, including via the cloud or a peer-to-peer network. The computer system may operate in the capacity of a server in a client-server network environment. The computer system may be a personal computer (PC), a tablet computer, a wearable (e.g., wristband), a set-top box (STB), a personal Digital Assistant (PDA), a mobile phone, a smartphone, a camera, a video camera, an Internet of Things (IoT) device, or any device capable of executing a set of instructions (sequential or otherwise) that specify actions to be taken by that device. Further, while only a single computer system is illustrated, the term "computer" shall also be taken to include any collection of computers that individually or jointly execute a set (or multiple sets) of instructions to perform any one or more of the methods discussed herein.

The computer system 1100 (one example of a "computing device") includes a processing device 1102, a main memory 1104 (e.g., read-only memory (ROM), flash memory, solid state drives (SSDs), dynamic random access memory (DRAM) such as synchronous DRAM (SDRAM)), a static memory 1106 (e.g., flash memory, solid state drives (SSDs), static random access memory (SRAM)), and a data storage device 1108, which communicate with each other via a bus 1110.

Processing device 1102 represents one or more general-purpose processing devices such as a microprocessor, central processing unit, or the like. More particularly, the processing device 1102 may be a complex instruction set computing (CISC) microprocessor, reduced instruction set computing (RISC) microprocessor, very long instruction word (VLIW) microprocessor, or a processor implementing other instruction sets or processors implementing a combination of instruction sets. The processing device 1402 may also be one or more special-purpose processing devices such as an application specific integrated circuit (ASIC), a system on a chip, a field programmable gate array (FPGA), a digital signal processor (DSP), network processor, or the like. The processing device 1402 may be configured to execute instructions for performing any of the operations and steps discussed herein.

The computer system 1100 may further include a network interface device 1112. The computer system 1100 also may include a video display 1114 (e.g., a liquid crystal display (LCD), a light-emitting diode (LED), an organic light-emitting diode (OLED), a quantum LED, a cathode ray tube (CRT), a shadow mask CRT, an aperture grille CRT, a monochrome CRT), one or more input devices 1116 (e.g., a keyboard and/or a mouse or a gaming-like control), and one or more speakers 1118 (e.g., a speaker). In one illustrative example, the video display 1114 and the input device(s) 1116 may be combined into a single component or device (e.g., an LCD touch screen).

The data storage device 1116 may include a computer-readable medium 1120 on which the instructions 1122 embodying any one or more of the methods, operations, or functions described herein is stored. The instructions 1122 may also reside, completely or at least partially, within the main memory 1104 and/or within the processing device 1102 during execution thereof by the computer system 1100. As such, the main memory 1104 and the processing device 1102 also constitute computer-readable media. The instructions 1122 may further be transmitted or received over a network via the network interface device 1112.

While the computer-readable storage medium 1120 is shown in the illustrative examples to be a single medium, the term "computer-readable storage medium" should be taken to include a single medium or multiple media (e.g., a centralized or distributed database, and/or associated caches and servers) that store the one or more sets of instructions. The term "computer-readable storage medium" shall also be taken to include any medium capable of storing, encoding or carrying out a set of instructions for execution by the machine and that cause the machine to perform any one or more of the methodologies of the present disclosure. The term "computer-readable storage medium" shall accordingly be taken to include, but not be limited to, solid-state memories, optical media, and magnetic media.

Any of the systems and methods described in this disclosure may be used in connection with rehabilitation. Unless expressly stated otherwise, is to be understood that rehabilitation includes prehabilitation (also referred to as "prehabilitation" or "prehab"). Prehabilitation may be used as a preventative procedure or as a pre-surgical or pre-treatment procedure. Prehabilitation may include any action performed by or on a patient (or directed to be performed by or on a patient, including, without limitation, remotely or distally through telemedicine) to, without limitation, prevent or reduce a likelihood of injury (e.g., prior to the occurrence of the injury); improve recovery time subsequent to surgery; improve strength subsequent to surgery; or any of the foregoing with respect to any non-surgical clinical treatment plan to be undertaken for the purpose of ameliorating or mitigating injury, dysfunction, or other negative consequence of surgical or non-surgical treatment on any external or internal part of a patient's body. For example, a mastectomy may require prehabilitation to strengthen muscles or muscle groups affected directly or indirectly by the mastectomy. As a further non-limiting example, the removal of an intestinal tumor, the repair of a hernia, open-heart surgery or other procedures performed on internal organs or structures, whether to repair those organs or structures, to excise them or parts of them, to treat them, etc., can require cutting through and harming numerous muscles and muscle groups in or about, without limitation, the abdomen, the ribs and/or the thoracic cavity. Prehabilitation can improve a patient's speed of recovery, measure of quality of life, level of pain, etc. in all the foregoing procedures. In one embodiment of prehabilitation, a pre-surgical procedure or a pre-non-surgical-treatment may include one or more sets of exercises for a patient to perform prior to such procedure or treatment. The patient may prepare an area of his or her body for the surgical procedure by performing the one or more sets of exercises, thereby strengthening muscle groups, improving existing and/or establishing new muscle memory, enhancing mobility, improving blood flow, and/or the like.

In some embodiments, the systems and methods described herein may use artificial intelligence and/or machine learning to generate a prehabilitation treatment plan for a user. Additionally, or alternatively, the systems and methods described herein may use artificial intelligence and/or machine learning to recommend an optimal exercise machine configuration for a user. For example, a data model may be trained on historical data such that the data model may be provided with input data relating to the user and may generate output data indicative of a recommended exercise machine configuration for a specific user. Additionally, or alternatively, the systems and methods described herein may use machine learning and/or artificial intelligence to generate other types of recommendations relating to prehabilitation, such as recommended reading material to educate the patient, a recommended medical professional specialist to contact, and/or the like.

Consistent with the above disclosure, the examples of systems and methods enumerated in the following clauses are specifically contemplated and are intended as a non-limiting set of examples.

Clause 1. A computer-implemented system, comprising: a treatment apparatus configured to be manipulated by a patient while the patient performs one or more treatment sessions; a patient interface comprising an output device and an input device, the input device configured to receive patient input correlating with at least one pain level of the patient during the one or more treatment sessions; and a computing device configured to: receive a treatment plan for the patient, wherein the treatment plan comprises one or more exercise routines for the patient to complete on the treatment apparatus during the one or more treatment sessions, receive treatment data pertaining to the patient, receive the patient input from the patient interface, use the treatment plan, the treatment data, and the patient input to generate at least one threshold, and responsive to an occurrence of exceeding the at least one threshold, modify the treatment plan using an artificial intelligence engine.

Clause 2. The computer-implemented system of any clause herein, wherein the treatment data comprises at least one of characteristics of the patient, measurement information pertaining to the patient while the patient uses the treatment apparatus, and characteristics of the treatment.

Clause 3. The computer-implemented system of any clause herein, wherein the computing device is further configured to control, based on the modified treatment plan, the treatment apparatus while the patient uses the treatment apparatus.

Clause 4. The computer-implemented system of any clause herein, wherein the computing device is further configured to control, based on the modified treatment plan, the treatment apparatus while the patient uses the treatment apparatus during a telemedicine session.

Clause 5. The computer-implemented system of any clause herein, wherein the computing device is further configured to: receive modified patient input correlating with an updated pain level of the patient; use the modified treatment plan, the treatment data, and the modified patient input to generate at least one modified threshold; and responsive to an occurrence of exceeding the at least one modified threshold, modify the modified treatment plan.

Clause 6. The computer-implemented system of any clause herein, wherein, to modify the treatment plan, the computing device is further configured to generate at least one updated exercise routine during one of the one or more treatment sessions.

Clause 7. A method for modifying, by an artificial intelligence engine, a treatment plan for optimizing patient outcome and pain levels during one or more treatment sessions, the method comprising: receiving the treatment plan for a patient, wherein the treatment plan comprises one or more exercise routines for the patient to complete during the one or more treatment sessions; receiving treatment data pertaining to the patient; receiving patient input correlating with at least one of the pain levels of the patient; using the treatment plan, the treatment data, and the patient input to generate at least one threshold; and responsive to an occurrence of exceeding the at least one threshold, modifying the treatment plan.

Clause 8. The method of any clause herein, wherein the treatment plan comprises the one or more exercise routines for the patient to perform on a treatment device.

Clause 9. The method of any clause herein, wherein the treatment data comprises at least one of characteristics of the patient, measurement information pertaining to the patient while the patient uses the treatment device, and characteristics of the treatment device.

Clause 10. The method of any clause herein, further comprising controlling, based on the modified treatment plan, the treatment device while the patient uses the treatment device.

Clause 11. The method of any clause herein, further comprising controlling, based on the modified treatment plan, the treatment device while the patient uses the treatment device during a telemedicine session.

Clause 12. The method of any clause herein, further comprising: receiving modified patient input correlating with an updated pain level of the patient; using the modified treatment plan, the treatment data, and the modified patient input to generate at least one modified threshold; and responsive to an occurrence of exceeding the at least one modified threshold, modifying the modified treatment plan.

Clause 13. The method of any clause herein, wherein modifying the treatment plan comprises generating at least one updated exercise routine during one of the one or more treatment sessions.

Clause 14. The method of any clause herein, wherein at least one of the treatment data and the patient input is received in real-time or near real-time; and wherein the treatment plan is modified in real-time or near real-time.

Clause 15. A tangible, non-transitory computer-readable medium storing instructions that, when executed, cause a processing device to: receive a treatment plan for a patient, wherein the treatment plan comprises one or more exercise routines for the patient to complete during one or more treatment sessions; receive treatment data pertaining to the patient; receive patient input correlating with at least one pain level of the patient during the one or more treatment sessions; use the treatment plan, the treatment data, and the patient input to generate at least one threshold; and responsive to an occurrence of exceeding the at least one threshold, modify the treatment plan.

Clause 16. The computer-readable medium of any clause herein, wherein the treatment plan comprises the one or more exercise routines for the patient to perform on a treatment device.

Clause 17. The computer-readable medium of any clause herein, wherein the treatment data comprises at least one of characteristics of the patient, measurement information pertaining to the patient while the patient uses the treatment device, and characteristics of the treatment device.

Clause 18. The computer-readable medium of any clause herein, wherein the processing device is further configured to control, based on the modified treatment plan, the treatment device while the patient uses the treatment device.

Clause 19. The computer-readable medium of any clause herein, wherein the processing device is further configured to control, based on the modified treatment plan, the treatment device while the patient uses the treatment device during a telemedicine session.

Clause 20. The computer-readable medium of claim any clause herein, wherein the processing device is further configured to: receive modified patient input correlating with an updated pain level of the patient; use the modified treatment plan, the treatment data, and the modified patient input to generate at least one modified threshold; and responsive to an occurrence of exceeding the at least one modified threshold, modify the modified treatment plan.

Clause 21. The computer-readable medium of any clause herein, wherein modifying the treatment plan comprises generating at least one updated exercise routine during one of the one or more treatment sessions.

Clause 22. The computer-readable medium of any clause herein, wherein at least one of the treatment data and the patient input is received in real-time or near real-time; and wherein the treatment plan is modified in real-time or near real-time.

Clause 23. A system for modifying, by an artificial intelligence engine, a treatment plan for optimizing patient outcome and pain levels during one or more treatment sessions, comprising: a memory device storing instructions; and a processing device communicatively coupled to the memory device, the processing device executes the instructions to: receive the treatment plan for a patient, wherein the treatment plan comprises one or more exercise routines for the patient to complete during the one or more treatment sessions; receive treatment data pertaining to the patient; receive patient input correlating with at least one of the pain levels of the patient; use the treatment plan, the treatment data, and the patient input to generate at least one threshold; and responsive to an occurrence of exceeding the at least one threshold, modify the treatment plan.

Clause 24. The system of any clause herein, wherein the treatment plan comprises the one or more exercise routines for the patient to perform on a treatment device.

Clause 25. The system of any clause herein, wherein the treatment data comprises at least one of characteristics of the patient, measurement information pertaining to the patient while the patient uses the treatment device, and characteristics of the treatment device.

Clause 26. The system of any clause herein, wherein the processing device is further configured to control, based on the modified treatment plan, the treatment device while the patient uses the treatment device.

Clause 27 The system of any clause herein, wherein the processing device is further configured to control, based on the modified treatment plan, the treatment device while the patient uses the treatment device during a telemedicine session.

Clause 28. The system of any clause herein, wherein the processing device is further configured to: receive modified patient input correlating with an updated pain level of the patient; use the modified treatment plan, the treatment data, and the modified patient input to generate at least one modified threshold; and responsive to an occurrence of exceeding the at least one modified threshold, modify the modified treatment plan.

Clause 29. The system of any clause herein, wherein modifying the treatment plan comprises generating at least one updated exercise routine during one of the one or more treatment sessions.

Clause 30. The system of any clause herein, wherein at least one of the treatment data and the patient input is received in real-time or near real-time; and wherein the treatment plan is modified in real-time or near real-time.

No part of the description in this application should be read as implying that any particular element, step, or function is an essential element that must be included in the claim scope. The scope of patented subject matter is defined only by the claims. Moreover, none of the claims is intended to invoke 25 U.S.C. § 104(f) unless the exact words "means for" are followed by a participle.

The foregoing description, for purposes of explanation, use specific nomenclature to provide a thorough understanding of the described embodiments. However, it should be apparent to one skilled in the art that the specific details are not required to practice the described embodiments. Thus, the foregoing descriptions of specific embodiments are presented for purposes of illustration and description. They are not intended to be exhaustive or to limit the described embodiments to the precise forms disclosed. It should be apparent to one of ordinary skill in the art that many modifications and variations are possible in view of the above teachings.

The above discussion is meant to be illustrative of the principles and various embodiments of the present invention. Once the above disclosure is fully appreciated, numerous variations and modifications will become apparent to those skilled in the art. It is intended that the following claims be interpreted to embrace all such variations and modifications.

What is claimed is:

1. A computer-implemented system, comprising:
a treatment apparatus configured to be manipulated by a patient while the patient performs one or more treatment sessions;
a patient interface comprising an output device and an input device, the input device configured to receive patient input correlating with at least one pain level of the patient during the one or more treatment sessions; and
a computing device configured to:
receive a treatment plan for the patient, wherein the treatment plan comprises one or more exercise routines for the patient to complete on the treatment apparatus during the one or more treatment sessions,
receive treatment data pertaining to the patient,
receive the patient input from the patient interface,
use the treatment plan, the treatment data, and the patient input to generate at least one threshold, and
responsive to an occurrence of exceeding the at least one threshold, modify the treatment plan using an artificial intelligence engine.

2. The computer-implemented system of claim 1, wherein the treatment data comprises at least one of characteristics of the patient, measurement information pertaining to the patient while the patient uses the treatment apparatus, and characteristics of the treatment.

3. The computer-implemented system of claim 1, wherein the computing device is further configured to control, based on the modified treatment plan, the treatment apparatus while the patient uses the treatment apparatus.

4. The computer-implemented system of claim 1, wherein the computing device is further configured to control, based on the modified treatment plan, the treatment apparatus while the patient uses the treatment apparatus during a telemedicine session.

5. The computer-implemented system of claim 1, wherein the computing device is further configured to:
receive modified patient input from the patient interface correlating with an updated pain level of the patient;
use the modified treatment plan, the treatment data, and the modified patient input to generate at least one modified threshold; and
responsive to an occurrence of exceeding the at least one modified threshold, modify the modified treatment plan.

6. The computer-implemented system of claim 1, wherein, to modify the treatment plan, the computing device is further configured to generate at least one updated exercise routine during one of the one or more treatment sessions.

7. A method for modifying, by an artificial intelligence engine, a treatment plan for optimizing patient outcome and pain levels during one or more treatment sessions, the method comprising:
receiving the treatment plan for a patient, wherein the treatment plan comprises one or more exercise routines for the patient to complete during the one or more treatment sessions;
receiving treatment data pertaining to the patient;
receiving patient input correlating with at least one of the pain levels of the patient;
using the treatment plan, the treatment data, and the patient input to generate at least one threshold; and
responsive to an occurrence of exceeding the at least one threshold, modifying the treatment plan.

8. The method of claim 7, wherein the treatment plan comprises the one or more exercise routines for the patient to perform on a treatment device.

9. The method of claim 8, wherein the treatment data comprises at least one of characteristics of the patient, measurement information pertaining to the patient while the patient uses the treatment device, and characteristics of the treatment device.

10. The method of claim 8, further comprising controlling, based on the modified treatment plan, the treatment device while the patient uses the treatment device.

11. The method of claim 8, further comprising controlling, based on the modified treatment plan, the treatment device while the patient uses the treatment device during a telemedicine session.

12. The method of claim 7, further comprising:
receiving modified patient input correlating with an updated pain level of the patient;
using the modified treatment plan, the treatment data, and the modified patient input to generate at least one modified threshold; and
responsive to an occurrence of exceeding the at least one modified threshold, modifying the modified treatment plan.

13. The method of claim 7, wherein modifying the treatment plan comprises generating at least one updated exercise routine during one of the one or more treatment sessions.

14. The method of claim 7, wherein at least one of the treatment data and the patient input is received in real-time or near real-time; and wherein the treatment plan is modified in real-time or near real-time.

15. A tangible, non-transitory computer-readable medium storing instructions that, when executed, cause a processing device to:
receive a treatment plan for a patient, wherein the treatment plan comprises one or more exercise routines for the patient to complete during one or more treatment sessions;
receive treatment data pertaining to the patient;
receive patient input correlating with at least one pain level of the patient during the one or more treatment sessions;
use the treatment plan, the treatment data, and the patient input to generate at least one threshold; and
responsive to an occurrence of exceeding the at least one threshold, modify the treatment plan.

16. The computer-readable medium of claim 15, wherein the treatment plan comprises the one or more exercise routines for the patient to perform on a treatment device.

17. The computer-readable medium of claim 16, wherein the treatment data comprises at least one of characteristics of the patient, measurement information pertaining to the patient while the patient uses the treatment device, and characteristics of the treatment device.

18. The computer-readable medium of claim 16, wherein the processing device is further configured to control, based on the modified treatment plan, the treatment device while the patient uses the treatment device.

19. The computer-readable medium of claim 16, wherein the processing device is further configured to control, based on the modified treatment plan, the treatment device while the patient uses the treatment device during a telemedicine session.

20. The computer-readable medium of claim 15, wherein the processing device is further configured to:
 receive modified patient input correlating with an updated pain level of the patient;
 use the modified treatment plan, the treatment data, and the modified patient input to generate at least one modified threshold; and
 responsive to an occurrence of exceeding the at least one modified threshold, modify the modified treatment plan.

21. The computer-readable medium of claim 15, wherein modifying the treatment plan comprises generating at least one updated exercise routine during one of the one or more treatment sessions.

22. The computer-readable medium of claim 15, wherein at least one of the treatment data and the patient input is received in real-time or near real-time; and wherein the treatment plan is modified in real-time or near real-time.

23. A system for modifying, by an artificial intelligence engine, a treatment plan for optimizing patient outcome and pain levels during one or more treatment sessions, comprising:
 a memory device storing instructions; and
 a processing device communicatively coupled to the memory device, the processing device executes the instructions to:
  receive the treatment plan for a patient, wherein the treatment plan comprises one or more exercise routines for the patient to complete during the one or more treatment sessions;
  receive treatment data pertaining to the patient;
  receive patient input correlating with at least one of the pain levels of the patient;
  use the treatment plan, the treatment data, and the patient input to generate at least one threshold; and
  responsive to an occurrence of exceeding the at least one threshold, modify the treatment plan.

24. The system of claim 23, wherein the treatment plan comprises the one or more exercise routines for the patient to perform on a treatment device.

25. The system of claim 24, wherein the treatment data comprises at least one of characteristics of the patient, measurement information pertaining to the patient while the patient uses the treatment device, and characteristics of the treatment device.

26. The system of claim 24, wherein the processing device is further configured to control, based on the modified treatment plan, the treatment device while the patient uses the treatment device.

27. The system of claim 24, wherein the processing device is further configured to control, based on the modified treatment plan, the treatment device while the patient uses the treatment device during a telemedicine session.

28. The system of claim 23, wherein the processing device is further configured to:
 receive modified patient input correlating with an updated pain level of the patient;
 use the modified treatment plan, the treatment data, and the modified patient input to generate at least one modified threshold; and
 responsive to an occurrence of exceeding the at least one modified threshold, modify the modified treatment plan.

29. The system of claim 23, wherein modifying the treatment plan comprises generating at least one updated exercise routine during one of the one or more treatment sessions.

30. The system of claim 23, wherein at least one of the treatment data and the patient input is received in real-time or near real-time; and wherein the treatment plan is modified in real-time or near real-time.

\* \* \* \* \*